US010507239B2

(12) United States Patent
Berman et al.

(10) Patent No.: US 10,507,239 B2
(45) Date of Patent: Dec. 17, 2019

(54) V1/V2 FRAGMENTS OF A HIV-1 ENVELOPE GLYCOPROTEIN

(71) Applicant: The Regents of the University of California, Oakland, CA (US)

(72) Inventors: Phillip Berman, Santa Cruz, CA (US); Gwen Tatsuno, Santa Cruz, CA (US); Bin Yu, Santa Cruz, CA (US); Javier Morales, Santa Cruz, CA (US); Kathryn Mesa, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1 day.

(21) Appl. No.: 15/635,064

(22) Filed: Jun. 27, 2017

(65) Prior Publication Data

US 2018/0036401 A1 Feb. 8, 2018

Related U.S. Application Data

(62) Division of application No. 14/427,393, filed as application No. PCT/US2013/059243 on Sep. 11, 2013, now Pat. No. 9,731,002.

(60) Provisional application No. 61/699,680, filed on Sep. 11, 2012.

(51) Int. Cl.

| | |
|---|---|
| ***A61K 39/12*** | (2006.01) |
| ***A61K 39/21*** | (2006.01) |
| ***C07K 14/005*** | (2006.01) |
| ***C07K 14/15*** | (2006.01) |
| ***C07K 14/16*** | (2006.01) |
| ***C12P 21/00*** | (2006.01) |

(52) U.S. Cl.

CPC .............. *A61K 39/21* (2013.01); *A61K 39/12* (2013.01); *C07K 14/005* (2013.01); *C07K 14/15* (2013.01); *C07K 14/162* (2013.01); *C12P 21/005* (2013.01); *C12N 2740/16034* (2013.01); *C12N 2740/16122* (2013.01); *C12N 2740/16134* (2013.01)

(58) Field of Classification Search

None

See application file for complete search history.

(56) References Cited

U.S. PATENT DOCUMENTS

| | | | |
|---|---|---|---|
| 2011/0311585 | A1 | 12/2011 | Berman |
| 2013/0101617 | A1 | 4/2013 | Binley |
| 2014/0335126 | A1 | 11/2014 | Haynes |

FOREIGN PATENT DOCUMENTS

| | | |
|---|---|---|
| WO | WO 2005/097822 | 10/2005 |
| WO | WO 2012/003234 | 1/2012 |

OTHER PUBLICATIONS

McLellan et al., Nature, Dec. 11, 2011, 480:336-345. (Year: 2011).*
Burton, et al.; "Why do we not have an HIV vaccine and how can we make one?" Nature Medicine Vaccine Supplement; vol. 4, No. 5, pp. 495-498 (May 1998).
Desrosiers; "Prospects for an AIDS vaccine"; Nature Medicine; vol. 10, No. 3, pp. 221-223 (Mar. 2004).
Matthews, et al.; "Prospects for Development of a Vaccine Against HTLV-III-Related Disorders"; AIDS Research and Human Retroviruses; vol. 3, No. 1, pp. 197-206 (1987).
Nakamura, et al.; "Monoclonal Antibodies to the V2 Domain of MN-rgp10: Fine Mapping of Epitopes and Inhibition of α4β7 Binding"; PLoS One; vol. 7, No. 6, 13 pages. (Jun. 2012).
Seaman, et al.; "Tiered Categorization of a Diverse Panel of HIV-1 Env Pseudoviruses for Assessment of Neutralizing Antibodies"; Journal of Virology; vol. 84, No. 3, pp. 1439-1452 (Feb. 2010).
Yang, et al.; "Selective Modification of Variable Loops Alters Tropism and Enhances Immunogenicity of Human Immunodeficiency Virus Type 1 Envelope"; Journal of Virology; vol. 78, No. 8, pp. 4029-4036 (Apr. 2004).
Yu, et al.; "Glycoform and Net Charge Heterogeneity in gp120 Immunogens Used in HIV Vaccine Trials"; PLoS One; vol. 7, No. 8, 10 pages (Aug. 2012).
Doores, et al.; "Variable Loop Glycan Dependency of the Broad and Potent HIV-1-Neutralizing Antibodies PG9 and PG16"; Journal of Virology; vol. 84, No. 20, pp. 10510-10521 (Oct. 2010).
Morales, et al.; "HIV-1 Envelope Proteins and V1/V2 Domain Scaffolds with Mannose-5 to Improve the Magnitude and Quality of Protective Antibody Responses to HIV-1"; Journal of Biological Chemistry; vol. 289, No. 30, pp. 20526-20542 (May 28 2014).
Pinter, et al.; "Potent neutralization of primary HIV-1 isolates by antibodies directed against epitopes present in the V1/V2 domain of HIV-1 gp120"; Vaccine; vol. 16, No. 19, pp. 1803-1811 (1998).
UniProtKB—4 pages (May 25, 2018).

* cited by examiner

*Primary Examiner* — Nicole Kinsey White
(74) *Attorney, Agent, or Firm* — Shweta Chandra; Bozicevic, Field & Francis LLP

(57) ABSTRACT

HIV-1 envelope proteins and fragments that possess naturally occurring and novel engineered epitopes that can be used to elicit (and are recognized by) broadly neutralizing antibodies.

12 Claims, 29 Drawing Sheets

Specification includes a Sequence Listing.

ELISA of PG9 binding to HIV-1 envelope proteins produced in normal and CH0, 293, and GNTI-293 cells. A-B, PG9 binding to A244-and MN -rgp 120 produced in CH0, 293, and GNTI-293 cells. C, PG9 binding to purified clade C gp120s expressed in 293 cells.

PG9 binding to fragments of MN- and A244-rgp 120 expressed in normal and GnTI-293 cells.

A, PG9 binding to fragments (2 µg/well) of MN-rgp120. B, PG9-like MAbs (PG9, PG16, CH01, CH03, and PGT145) binding to the V1/V2 scaffold of A244-rgp120. C, diagram of A244-V1/V2 scaffold expressed with a gD flag epitope and signal sequence.

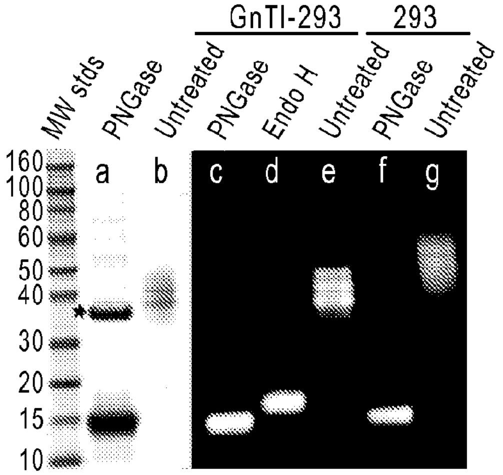

FIG. 3A

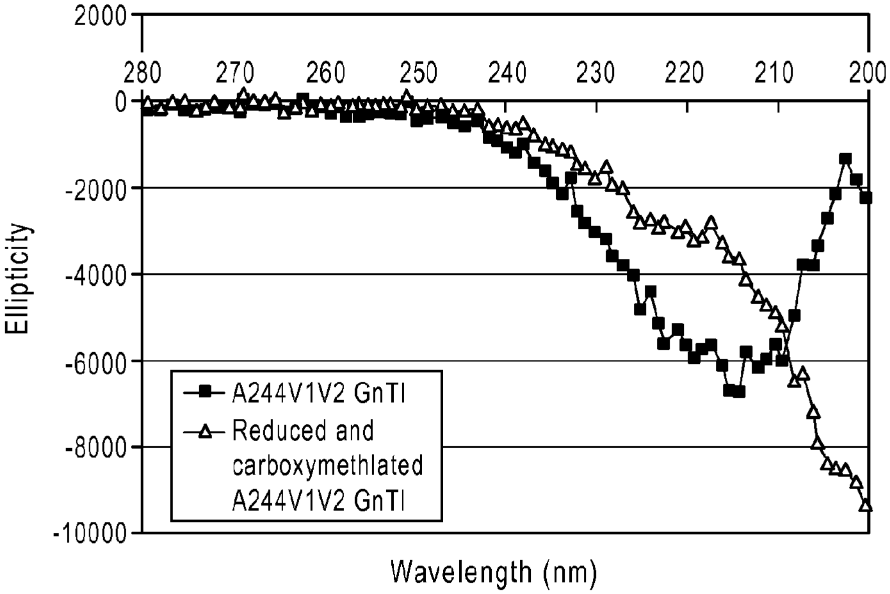

FIG. 3B

PAGE and circular dichroism analysis of the A244 V1/V2 scaffold produced in GNTI-293 cells. A, Purified A244-V1/V2 scaffold was analyzed by SDS-PAGE and resolved on 4 to 12% gels. Lanes a and b represent a Coomassie-stained gel of purified scaffold before (untreated) or after PNGase digestion. The band corresponding to PNGase is indicated by an asterisk. Lanes c-g represent immunoblots of the A244-V1/V2 scaffold expressed in normal or GNTI-203 cells before (untreated) and after digestion with endoglycosidase H (Endo H) or PNGase. Proteins were detected with the 34.1 monoclonal antibody to the gD flag epitiope. B, Circular dichroism of purified A244-V1/V2 scaffold produced in GNTI-293 cells (1 mg/mL) before and after denaturation by reduction and carboxymethylation.

Binding of PG9 amd PGT128 to variants of MN-rgp120 with glycosylation sites added to the V3 stem.

A, listing of MN-rgp120 glycosylation mutants.

B, ELISA of PG9 binding to purified gp120 from the MN and A244 strains expressed in GNTI-cells and MN expressed in normal 293 cells.

C, EUSA of PG9 binding to unpurified MN-rgp120 glycosylation mutants expressed in supernatants from normal 293 cells. The amount of protein in each experiment was normalized by quantitation with the 34.1 MAb to the gD flag epitope.

D, ELISA of PGT128 binding to the purified 468 MN-rgp120 glycosylation mutant expressed in normal 293 cells compared to A244 and MN-rgp120 ecpressed in wild type and GnTI-293 cells.

SEQ ID No. 1 = A244
SEQ ID No. 2 = MN533
SEQ ID No. 3 = MN470
SEQ ID No. 4 = MN471
SEQ ID No. 5 = MN467
SEQ ID No. 6 = MN468
SEQ ID No. 7 = MN469

FIG. 4A

```
      280       289         301 303                         332 334 336   348
A244  NNAKTIIVHLNKSVVINCTRPSNNTRTSITIGPGQVFYRTGDIIGDIRKAYCEINGTEWNKALKQVTEK
MN533 DNAKTIIVHLKESVQINCTRPNYNKRKRIHIGPGRAFYTTKNIKGTIRQAHCIISRAKWNDTKRQIVSK
470   ----------------------------------------------------N----------------
471   ------------------------------------------------------N-T------------
467   ----------N-----------N-T--------------------------------------------
468   ----------N-----------N-T---------------------------N----------------
469   ----------N-----------N-T-----------------------------N-T------------
```

FIG. 4B

108060 V3 Scaffold

UCSC 320

UCSC 321

UCSC 322

UCSC 324

UCSC 327

UCSC 328

Clade B: Tier 1B

UCSC588 A244V1V2 with gD flag epitope

MGGAAARLGAVILFVVIVGLHGVRGKYALADASLKMADPNRFRGKDLPVLDQLLEVPSVKLTPPCV
TLHCTNANLTKANLTNVNNRTNVSNIIGNITDEVRNCSFNMTTELRDKKQKVHALFYKLDIVPIED
NNDSSEYRLINCNTSVIKQA+

—— HSV signal sequence
------ gD flag epitope
-------- linker
........ Kpn1 cloning site
—–—– A244-V1/V2 sequence A244 Scaffold Sequence – A244V1V2 with gD flag epitope (SEQ ID No. 8)

FIG. 11A

UCSC596 A244V1V2 without a gD flag and with His tag

MGGAAARLGAVILFVVIVGLHGVRGTDNLWVTVYYGVPSVKLTPPCVTLHCTNANLTKANLTNVNN
RTNVSNIIGNITDEVRNCSFNMTTELRDKKQKVHALFYKLDIVPIEDNNDSSEYRLINCNTSVIKQ
ASGRHHHHHH+

—— HSV signal sequence
–·–·– 11 amino acids from the mature N-terminus of gp120
........ Kpn1 cloning site
–––– A244-V1/V2 sequence with 6 His residues at C terminus A244 Scaffold Sequence with gD flag epitope and His tag (SEQ ID No. 9)

FIG. 11B

SEQ ID No. 10

>ZM233M.PB6, SVPC9 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAGCCATGTGTAAAGTTGACCCCACTCTGTGTCACTTTGGATTGTAGTACCT
ACAATAATACCCACAATATTAGTAAGGAGATGAAAATTTGCTCTTTCAATATGACCACAGAACTAAGAGATAAGAA
ACGGAAAGTGAATGTACTTTTTTATAAACTTGATTTAGTGCCACTTACCAATTCTAGCAATACTACCAATTATAGATT
AATAAGTTGTAATACTTCAACCATAACACAAGCCTGTCCAAAGTAG

Fig. 12a

SEQ ID No. 11

> ZM109F.PB4, SVPC13 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAGCCATGTGTAAAATTGACCCCACTCTGTGTCACTTTAAATTGTACAAGTCC
TGCTGCCCACAATGAGAGCGAGACAAGAGTAAAACATTGCTCTTTCAATATAACCACAGATGTAAAAGATAGAAA
ACAGAAGGTGAATGCAACTTTTTATGACCTTGATATAGTACCACTTAGCAGCTCTGACAACTCTAGCAACTCTAGTC
TGTATAGATTAATAAGTTGTAATACCTCAACCATAACACAAGCCTGTCCAAAGTAG

Fig. 12b

SEQ ID No. 12

>CAP45.2.00.G3, SVPC16 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAGCCATGTGTAAAGTTGACCCCACTCTGTGTCACTTTAAGGTGTACAAATG
CTACTATTAATGGTAGCCTGACGGAAGAAGTAAAAAATTGCTCTTTCAATATAACCACAGAGCTAAGAGATAAGAA
ACAGAAAGCGTATGCACTTTTTTATAGACCTGATGTAGTACCACTTAATAAGAATAGCCCTAGTGGGAATTCTAGT
GAGTATATATTAATAAATTGCAATACCTCAACCATAACACAAGCCTGTCCAAAGTAG

Fig. 12c

SEQ ID No. 13

>Bal.01 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAGCCATGTGTAAAATTAACCCCACTCTGTGTTACTTTAAATTGCACTGATTT
GAGGAATGCTACTAGTAGGAATGTTACTAATACCACTAGTAGTAGCAGGGGAATGGTGGGGGGAGGAGAAATGA
AAAATTGCTCTTTCAATATCACCACAGGCATAAGAGGTAAGGTGCAGAAAGAATATGCACTTTTTTATGAACTTGA
TATAGTACCAATAGATAATAAAATTGATAGATATAGGTTGATAAGTTGTAACACCTCAGTCATTACACAGGCCTGT
CCAAAGTAG

Fig. 12d

SEQ ID No. 14

>ZM197M.PB7, SVPC6 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAGCCCTGTGTAAAGCTGACCCCACTCTGTGTCACTTTAAATTGTAGTGATG
CTACCAGTAATACTACCAAAAATGCTACCAATACTAATACCACCAGTACAGATAACAGAAATGCTACCAGTAATGA
TACTGAAATGAAGGGAGAAATAAAAGATTGCACTTTCAATATAACCACAGAAGTAAGAGATAGGAAGACAAAAC
AAAGGGCACTTTTTTATAAACTTGATGTAGTGCCACTTGAGGAGGAAAAGAATAGCTCTAGTAAAAATAGTAGCTA
TAAGGAGTATAGATTAATAAGTTGTAATACCTCAACCATAACACAAGCCTGTCCAAAGTAG

Fig. 12e

SEQ ID No. 15

>ZM53M.PB12, SVPC11 V1/V2 DNA sequence

ATGGGGGGGGCTGCCGCCAGGTTGGGGGCCGTGATTTTGTTTGTCGTCATAGTGGGCCTCCATGGGGTCCGCGG
CAAATATGCCTTGGCGGATGCCTCTCTCAAGATGGCCGACCCCAATCGATTTCGCGGCAAAGACCTTCCGGTCCTG
GACCAGCTGCTCGAGGTACCACTAAAACCATGTGTAAAATTGACCCCACTCTGTGTCACTTTAAACTGCAGCAAGC
TTAATAATGCCACGGATGGAGAAATGAAAAATTGCTCTTTCAATGCAACCACAGAACTAAGAGATAAGAAAAAGC
AAGTGTATGCACTTTTTTATAAACTTGATATAGTACCACTTGATGGAAGAAATAACTCTAGTGAGTATAGATTAATA
AATTGTAATACCTCAACCATAACACAAGCCTGTCCAAAGTAG

Fig. 12f

SEQ ID No. 16

> ZM233M.PB6, SVPC9 V1/V2 Protein sequence

MGGAAARLGAVILFVVIVGLHGVRGKYALADASLKMADPNRFRGKDLPVLDQLLEVPLKPCVKLTPLCVTLDCSTYNNT
HNISKEMKICSFNMTTELRDKKRKVNVLFYKLDLVPLTNSSNTTNYRLISCNTSTITQACPK*

Fig. 13a

SEQ ID No. 17

> ZM109F.PB4, SVPC13 V1/V2 Protein sequence

MGGAAARLGAVILFVVIVGLHGVRGKYALADASLKMADPNRFRGKDLPVLDQLLEVPLKPCVKLTPLCVTLNCTSPAAH
NESETRVKHCSFNITTDVKDRKQKVNATFYDLDIVPLSSSDNSSNSSLYRLISCNTSTITQACPK*

Fig. 13b

SEQ ID No. 18

>CAP45.2.00.G3, SVPC16 V1/V2 Protein sequence

MGGAAARLGAVILFVVIVGLHGVRGKYALADASLKMADPNRFRGKDLPVLDQLLEVPLKPCVKLTPLCVTLRCTNATIN
GSLTEEVKNCSFNITTELRDKKQKAYALFYRPDVVPLNKNSPSGNSSEYILINCNTSTITQACPK*

Fig. 13c

SEQ ID No. 19

>Bal.01 V1/V2 Protein sequence

MGGAAARLGAVILFVVIVGLHGVRGKYALADASLKMADPNRFRGKDLPVLDQLLEVPLKPCVKLTPLCVTLNCTDLRNA
TSRNVTNTTSSSRGMVGGGEMKNCSFNITTGIRGKVQKEYALFYELDIVPIDNKIDRYRLISCNTSVITQACPK*

SEQ ID No. 20

>ZM197M.PB7, SVPC6 V1/V2 Protein sequence

MGGAAARLGAVILFVVIVGLHGVRGKYALADASLKMADPNRFRGKDLPVLDQLLEVPLKPCVKLTPLCVTLNCSDATSN
TTKNATNTNTTSTDNRNATSNDTEMKGEIKDCTFNITTEVRDRKTKQRALFYKLDVVPLEEEKNSSSKNSSYKEYRLISCN
TSTITQACPK*

Fig. 13e

SEQ ID No. 19

>Bal.01 V1/V2 Protein sequence

MGGAAARLGAVILFVVIVGLHGVRGKYALADASLKMADPNRFRGKDLPVLDQLLEVPLKPCVKLTPLCVTLNCTDLRNA
TSRNVTNTTSSSRGMVGGGEMKNCSFNITTGIRGKVQKEYALFYELDIVPIDNKIDRYRLISCNTSVITQACPK*

Fig. 13f

SEQ ID No. 21

>ZM53M.PB12, SVPC11 V1/V2 Protein sequence

MGGAAARLGAVILFVVIVGLHGVRGKYALADASLKMADPNRFRGKDLPVLDQLLEVPLKPCVKLTPLCVTLNCSKLNNA
TDGEMKNCSFNATTELRDKKKQVYALFYKLDIVPLDGRNNSSEYRLINCNTSTITQACPK*

Fig. 13g

ELISA Data of PG9 binding to V1/V2 scaffolds produced in
293 Freestyle™ cells and 293-GnT1- cells Fragments expressed in 293F

| UCSC# | Strain (V1/V2) |
|---|---|
| 1006 | Bal.01 |
| 1007 | CAP.45 |
| 1008 | JR-CSF |
| 1009 | REJO |
| 1010 | SC422 |
| 1011 | WITO |
| 1012 | ZM53 |
| 1013 | ZM109 |
| 1014 | ZM197 |
| 1015 | ZM233 |

Fragments expressed in Gnt1 (-)

| UCSC# | Strain (V1/V2) |
|---|---|
| 1006 | Bal.01 |
| 1007 | CAP.45 |
| 1008 | JR-CSF |
| 1009 | REJO |
| 1010 | SC422 |
| 1011 | WITO |
| 1012 | ZM53 |
| 1013 | ZM109 |
| 1014 | ZM197 |
| 1015 | ZM233 |

PG9 Binding
(Indirect ELISA Format)

6. Develop — 10min.

(Wash)

5. Anti-human HRP (Fc) 1/5,000 — Incubate for 1hr.

(Wash)

4. PG9 (10ug/ml→0.001ug/ml) — Incubate for 1hr.

(Wash)

3. 100ul of V1/V2 supernatant — Incubate for 1hr.

2. Block — Block for 2hrs at RT.

(Wash)

1. Anti-gD @ 2ug/ml (34.1) — Coat overnight at 4°C

V1/V2 Fragments:

V1/V2 FRAGMENTS OF A HIV-1 ENVELOPE GLYCOPROTEIN

RELATIONSHIP TO PRIOR APPLICATIONS

This international application claims the benefit of and priority to U.S. provisional application No. 61/699,680 filed 11 Sep. 2012, titled "HIV-1 envelope proteins and fragments that possess glycan dependent epitopes recognized by broadly neutralizing antibodies" which is hereby incorporated by reference for all purposes.

STATEMENT OF GOVERNMENT SUPPORT

This invention was made with support of [no known government support]

FIELD OF THE INVENTION

Vaccines with an immunologically protective effect against HIV infection.

BACKGROUND

A major goal of HIV-1 vaccine development is to discover immunogens able to elicit broadly neutralizing antibodies (bNAbs). After more than 25 years of effort, none of the vaccines developed to date have been able to elicit antibodies of this type. For the last decade, the inability to elicit bNAbs has been assumed to result from our lack of success in accurately replicating the trimeric envelope proteins (gp120 and gp41) that compose viral spikes on the virus surface.

Over the last few years, data has emerged suggesting that broadly neutralizing antibodies recognize glycan-dependent epitopes in the HIV-1 envelope protein, gp120 rather than epitopes consisting only of amino acids. More recently, several 3-D structures of broadly neutralizing antibodies binding to HIV-1 envelope proteins have been solved. These have shown that as much as 77% of the binding surface recognized by selected broadly neutralizing monoclonal antibodies (bN-MAbs) is composed of carbohydrate.

Moreover these studies show that the epitope recognized by the prototypic PG9 MAb (16) was located in the V1/V2 domain of gp120 and dependent on mannose-5 for binding. Similarly, another epitope recognized by the prototypic MAb PGT128 (15) is located at the stem of V3 loop and depended on mannose-9 for binding.

Since these bN-MAbs exhibit little if any binding to monomeric gp120, but exhibit robust binding to trimeric envelopes on the surface of cells or viruses, these antibodies were thought to recognize epitopes dependent on both carbohydrate and on the quaternary structure of the envelope trimers (8, 15). Studies of the ontogeny of PG9-like antibodies (3) demonstrated the germline precursor of PG9 and PG9-like antibodies are unable to bind to most monomeric gp120 proteins.

However, one notable exception was gp120 from the A244 strain of HIV-1. Our lab originally determined the sequence of this virus in the early 1990s (7) and has worked with this protein for many years. Indeed this protein was a major component of the AIDSVAX B/E vaccine developed at Genentech and then licensed to VaxGen (1, 2). This vaccine failed to provide protection (11) in a Phase 3 trial (VAX003) carried out in Thailand (1998-2003). However modest but significant protection (31.4% efficacy) was achieved when this vaccine was combined with another vaccine vCP1521 in the RV144 trial involving more than 16,000 volunteers that ended in 2009 (12).

BRIEF DESCRIPTION OF THE INVENTION

The inventors have discovered that almost any monomeric gp120 will bind to PG9 provided it has the glycosylation sites at positions 156 and 160 that are not glycosylated or are only partially glycosylated, and the right amino acids in the area around amino acids 166-173. The inventors have data from several isolates and novel synthetic constructs showing this to be the case. The present consensus among HIV scientists is that gp120 binds better to trimers because of quaternaty interactions. The inventors have shown this is incorrect—almost any gp120 will bind if its produced in GNT1(−) cells. Our data suggests that PG9 binds better to trimers because the formation of trimers inside the cell shields positions 156 and 160 from interactions with glycoprocessing enzymes resulting in incomplete glycosylation at positions 156 and 160. Most monomeric proteins are not shileded from these enzymes and hence acquire the fully mature complex type of carbohdrate that is not recognized by PG9. Thus the incomplete glycosylation resulting from trimerization accounts for the preferential binding of PG9 to trimers and not the presence of an epitope dependent on quaternary interactions.

The present invention is based upon the reasoning that the best way to improve the immune response to PG9-like epitopes would be to develop small properly glycosylated glycoprotein fragments, or 'scaffolds' that possess the carbohydrate structures that the inventors discovered are required for the PG9 binding, and combine these with other Env proteins or other scaffolds to create a multivalent vaccine cocktail.

The invention encompasses small glycosylated fragments of HIV gp120 V1/V2 antigens (scaffolds) that possess the carbohydrate structures required for the PG9 binding. The invention additionally comprises combinations of such scaffolds with other Env proteins or other scaffolds to create a multivalent vaccine cocktail.

The invention encompasses a vaccine comprising a V1/V2 glycoprotein fragment scaffold produced in a cell line, for example A244 strain of HIV-1, or in other embodiments, two or more strains of HIV, where glycosylation is limited to glycosylation of mannose-5, and where the scaffold possesses an epitope in the V1/V2 domain recognized by the PG9 MAb.

The V1/V2 scaffold may be expressed in any strain of HIV-1 produced in a cell line where glycosylation is limited to mannose-5, and wherein the scaffold possesses the epitope in the V1/V2 domain recognized by the PG9 MAb.

The vaccine may comprise V1/V2 scaffolds from two or more strains of HIV-1 produced in a cell line where glycosylation is limited to mannose-5 and wherein the scaffold possesses the epitope in the V1/V2 domain recognized by the PG9 MAb.

In various embodiments the scaffolds may be conjugated to an immunogenic carrier protein.

In another embodiment a vaccine may comprise a mixture of gp120 and the V1/V2 scaffolds where both components are produced under conditions where mannose-5 is incorporated in the V1/V2 domain, and both components are capable of binding to the PG9 MAb.

Additionally, one or both components are derived from the A244 strain of HIV-1.

Where two or more immunogenic components are employed, for example a mixture of gp120 and the V1/V2 scaffolds, the components may be introduced to the subject simultaneously and both components may be contained in the same formulation and immunized at the same time.

Alternatively the components may be formulated separately and immunizations may be given at different times (prime/boost protocol).

Another embodiment comprises an envelope gene from MN-rgp120 mutated to incorporate N-linked glycosylation sites at positions 289, 301, 332 and/or 334 that possesses the epitopes recognized by both the PG9 and PGT128 MAbs when expressed in normal 293 cells. (MN-rgp120 is a recombinant gp120 that was a major component of the AIDSVAX B/E vaccine used in the RV144 trial).

In another embodiment the vaccine formulation is based on recombinant gp120 from the envelope gene from MN-rgp120 mutated to incorporate N-linked glycosylation sites at positions 289, 301, 332 and/or 334 that possesses the epitopes recognized by both the PG9 and PGT128 MAbs when expressed in normal 293 cells.

A related embodiment further comprises a V1/V2 scaffold produced under conditions where mannose-5 is incorporated in the V1/V2 domain, and both components are capable of binding to the PG9 MAb.

In an alternative embodiment the vaccine comprises a mixture of gp120 from the envelope gene from MN-rgp120 mutated to incorporate N-linked glycosylation sites at positions 289, 301, 332 and/or 334 that possesses the epitopes recognized by both the PG9 and PGT128 MAbs when expressed in normal 293 cells and a V1/V2 scaffold from the A244 strain of HIV-1 capable of binding the PG9 MAbs and produced under conditions where mannose-5 is incorporated in the V1/V2 domain and both components are capable of binding to the PG9 MAb and administered concurrently, or alternatively, sequentially, in a prime/boost strategy.

In another embodiment a subject would be immunized with monomeric gp120s possessing both the PG9 and PGT128 epitopes (for example the MN gp120 glycosylation mutant UCSC468) followed by boosting with a V1/V2 fragment that binds PG9 and a V3 fragment that binds PGT128.

Certain embodiments include a composition comprising a monomeric gp120 with glycosylation sites at positions 156 and 160. In various embodiments gp120 is produced in GNT1(−) cells.

BRIEF DESCRIPTION OF THE FIGURES

FIGS. 3A-3B PAGE and circular dichroism analysis of A244 and V1/V2 scaffold.

FIGS. 4A-4E Binding of PG9 and PGT128 antibodies to MN-rgp 120.

FIGS. 11A-11B Sequence of the two A244 V1/V2 scaffolds that give good binding to the PG9 MAb.

FIGS. 12*a*-12*f* show the polynucleotide sequences of V1/V2 scaffolds that bind PG9 (in FASTA format).

FIGS. 13*a*-13*g* show the primary amino acid sequences of V1/V2 scaffold proteins. These include specific, novel, synthetic sequences (some of which comprise the V1/V2 domain linked to a signal sequence) that show enhanced stability, enhanced binding and a decreased requirement for two glycan binding.

GENERAL REPRESENTATIONS CONCERNING THE DISCLOSURE

Figure 1A:
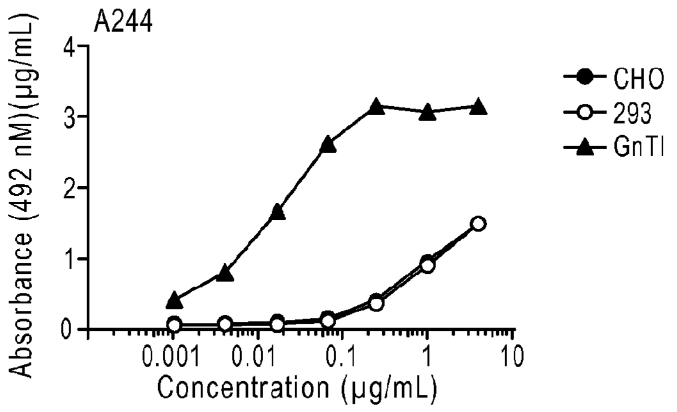
FIGS. 1A-1C ELISA of PG9 binding to envelope proteins.
Figure 1B:
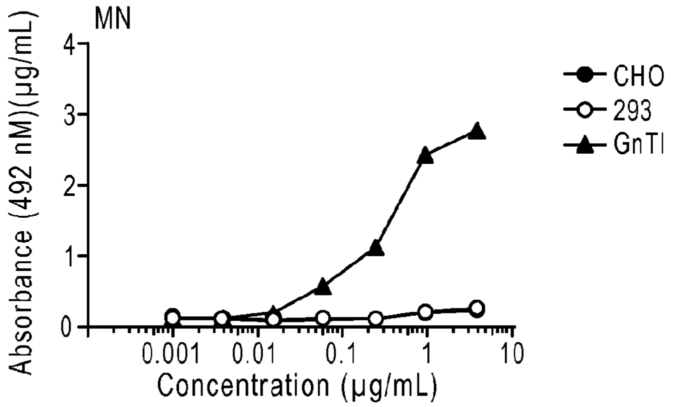

Incorporation by reference: U.S. provisional application No. 61/699,680 filed 11 Sep. 2012 is hereby incorporated by reference for all purposes, as are all documents referred to in the provisional application and in the present disclosure.

The terms “complementary” and “complementarity” refer to the natural binding of polynucleotides by base pairing. For example, the sequence “5' A-G-T 3'” bonds to the complementary sequence “3' T-C-A 5'.” Complementarity between two single-stranded molecules may be “partial,” such that only some of the nucleic acids bind, or it may be “complete,” such that total complementarity exists between the single stranded molecules. The degree of complementarity between nucleic acid strands has significant effects on the efficiency and strength of the hybridization between the nucleic acid strands.

The term “antisense” refers to any composition containing a nucleic acid sequence which is complementary to the “sense” strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation “negative” or “minus” can refer to the antisense strand, and the designation “positive” or “plus” can refer to the sense strand.

“Conservative amino acid substitutions” are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |

-continued

| Original Residue | Conservative Substitution |
|---|---|
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of a parent sequence which is identical in sequence to but shorter in length than the parent sequence. A fragment may comprise up to the entire length of the defined sequence, minus one nucleotide/amino acid residue. For example, a fragment may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single stranded or double stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

DETAILED DESCRIPTION OF THE INVENTION

A major goal in HIV vaccine research is the identification of antigens able to elicit the production of broadly neutralizing antibodies (bNAbs) effective against primary isolates of HIV. The applicant has investigated the molecular features of the HIV-1 envelope glycoproteins, gp160, gp120 and gp41, particularly the epitopes recognized by the prototypic PG9 MAb located in the V1/V2 domain, that confer sensitivity and resistance of viruses to neutralization.

Experimental Results

Based on reports that A244-rgp120 was able to bind PG9, the inventors analyzed archival specimens of A244 and MN-rgp120 from the AIDSVAX B/E vaccine to see if they may have failed to provide protection because they lacked the epitopes and carbohydrate required for the binding of the PG9 and PGT128 MAbs. The inventors found weak binding to A244-rgp120 and no binding to MN-rgp120. The inventors also found that both proteins were highly heterogeneous with respect to glycosylation, with the majority of carbohydrate being the complex, sialic acid-containing form that should not bind either MAb (17). To see if the inventors could improve the binding to monomeric gp120, the inventors produced monomeric gp120 from 3 strains of virus (MN, TR011 and A244) in a cell line that lacks the enzyme N-acetylglucosaminyltransferase I (GnTI) that results in mannose-5 glycans being incorporated at all of the predicted N-linked glycosylation sites (PNGS). When grown in normal 293 cells, MN-rgp120 and TRO11-rgp120 were unable to bind to PG9, and A244-rgp120 exhibited weak binding to PG9 (FIGS. 1A and B). However, when these proteins were expressed in the GnTI cells, all three proteins bound with high affinity to PG9. These results unambiguously demonstrated that monomeric gp120 could bind to PG9, provided that the proper glycosylation was present, and that trimeric envelope proteins were not required for binding of this antibody. This idea was published in our 2012 PLoS One publication (17).

There has been a considerable amount debate about the heterogeneity and nature of glycosylayion of V1/V2 proteins. Our protein produced in GNTI-cells show 3 major binds and all are due to differences in the occupancy of glycosylation sites. Thus all 3 bands collapse to a single band when deglycosylated by treatment with PNGase which removes all of the N-linked carbohydrate or Endo H that removes all of the high mannose carbohydtare (including mannose 5 glycans). The inventors know from mass spectroscopy studies that the 3 bands are due to differences in glycosylation site occupancy. These studies show that all 3 bands possess the carbohydrate at positions 156 and 160 required for the binding of PG9. These studies, carried out in our lab, used LC-MS/MS. The inventors also carried out disulfide mapping studies of the A244 V1/V2 fragment expressed in GNTI-cells. The inventors found that there was considerable disulfide heterogeneity, which in some preparations may be as high as 50%. The inventors would imagine that this would effect PG9 binding, but have not yet studies this.

Development of Scaffolds from the V1/V2 Domain that Binds Glycan-Dependent bN-MAbs.

Figure 6A:
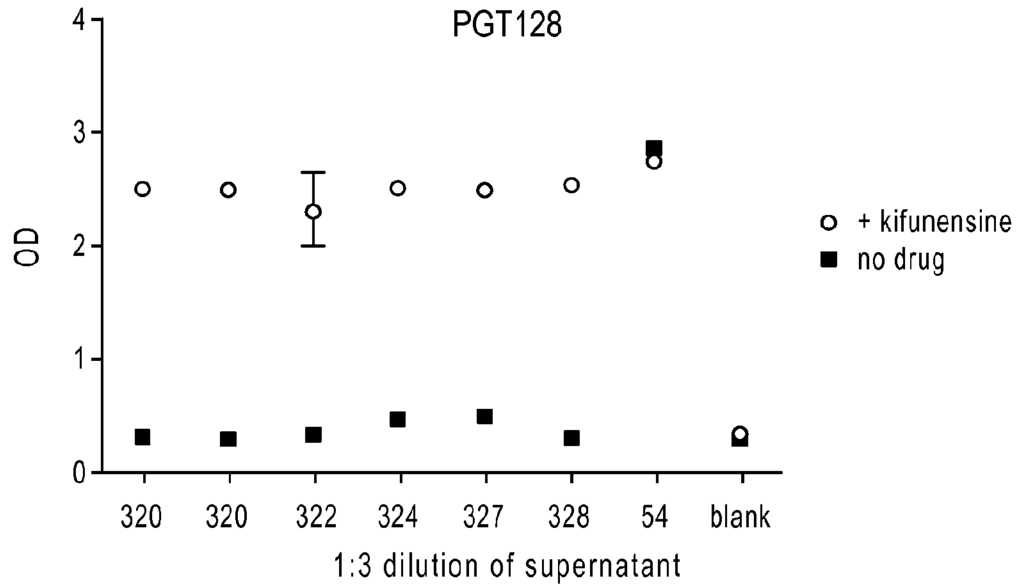
FIGS. 6A-6B depict competition for binding to monoclonal antibodies PGT128 (FIG. 6A) or 2G12 (FIG. 6B) by dilutions of supernatant from cells producing a V3 scaffold (FIG. 6B), where the cells were grown in the presence or absence of kifunensine.
Figure 6B:
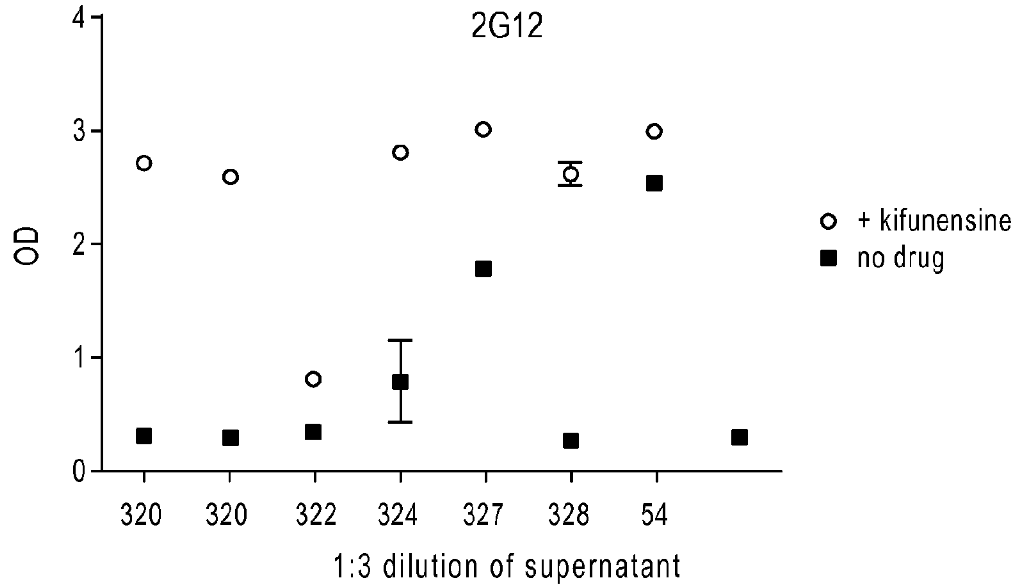
Figures 1, 6C:
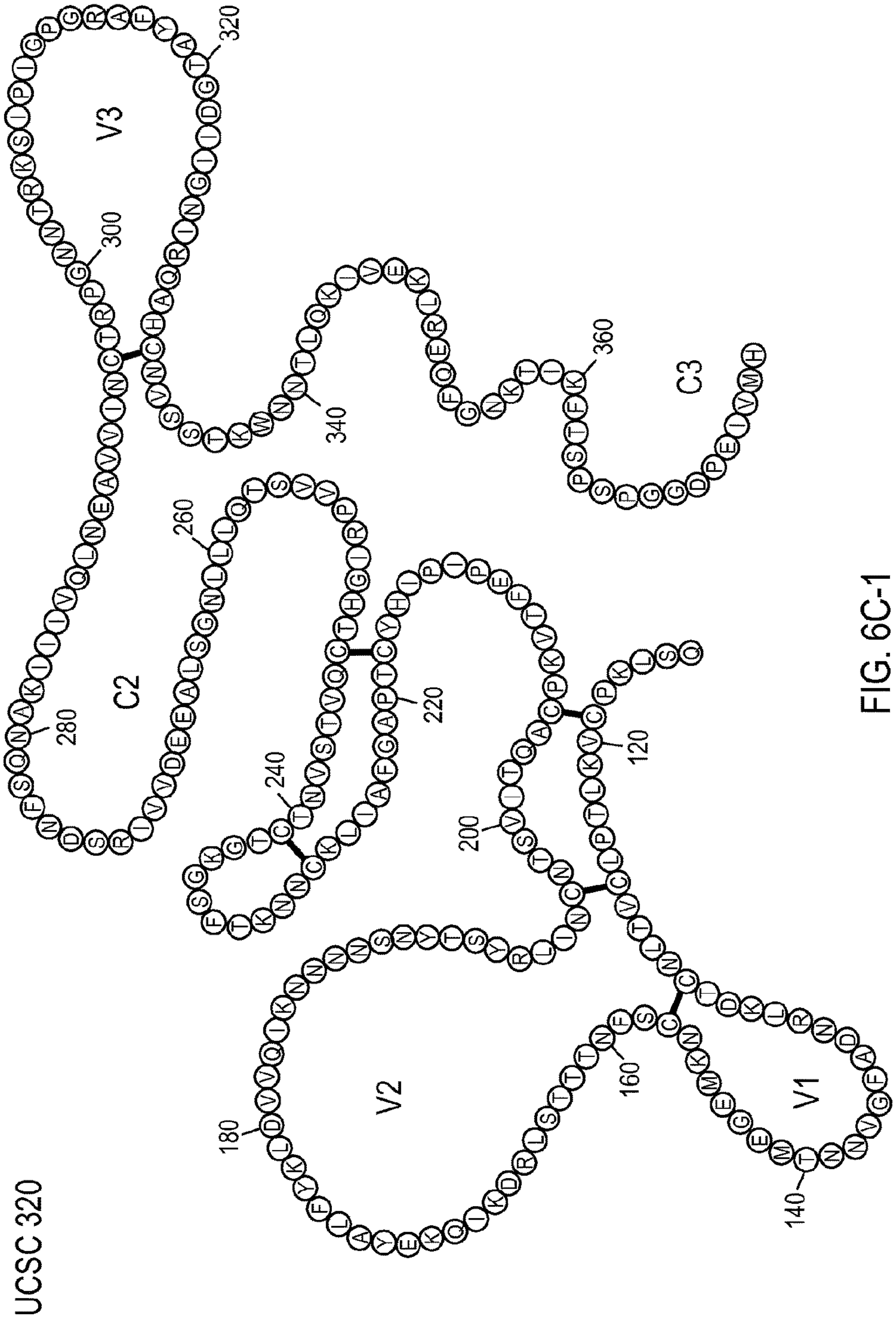
FIGS. 6C-1 to 6C-6 depict amino acid sequences of various gp120 variants.
Figures 2, 6C:
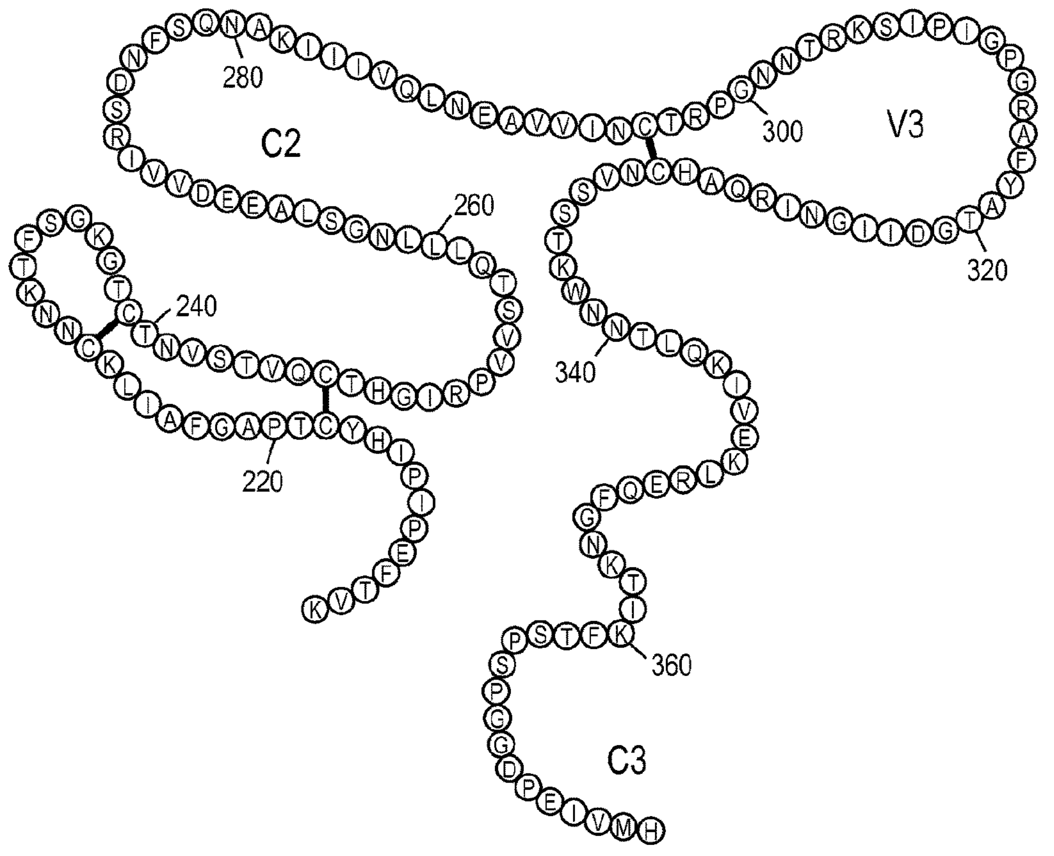

While expression of gp120 in GnTI-cells can greatly improve the binding by PG9-like antibodies, this method of production results in major changes in the biophysical and pharmacokinetic profile that could jeopardize the protective immunity achieved in the RV144 trial. Ideally, the inventors would like to add to the existing efficacy of AIDSVAX B/E rather than begin the development of a new vaccine from scratch. See FIG. 1.

One way the inventors could accomplish this is to supplement the AIDSVAX vaccine with other Env proteins produced in GnTI-cells. However, the antibody response to gp120 is very complex and only a small percentage of the overall antibody response to any Env protein produced in GnTI-cells would be directed to the PG9 epitope. Moreover, production of Envs in GnTI-cells would destroy other important neutralizing epitopes such as those recognized by PGT128 and 2G12 that depend on mannose-9 glycosylation for binding (10, 15). Therefore the inventors reasoned that the best way to improve the immune response to PG9-like epitopes would be to develop small properly glycosylated fragments, or scaffolds, that possessed the carbohydrate structures required for the PG9 binding, and combine these with other Env proteins or other scaffolds to create a multivalent vaccine cocktail.

Figure 2A:
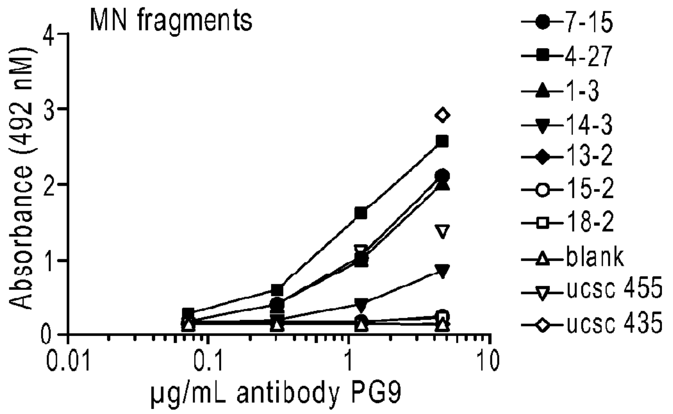
FIGS. 2A-2C PG9 binding to gp120 fragments.
Figure 2B:
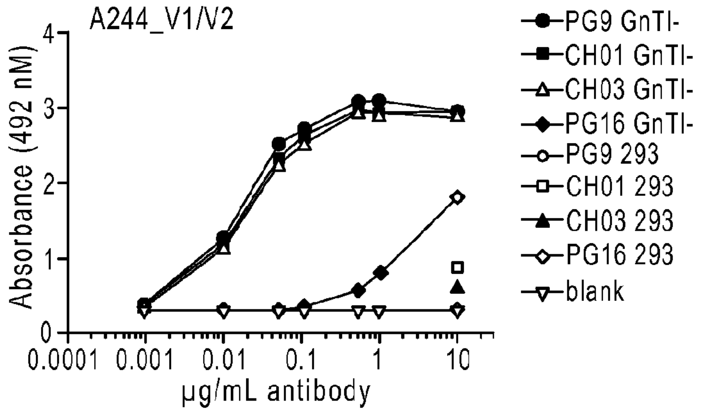
Figure 2C:
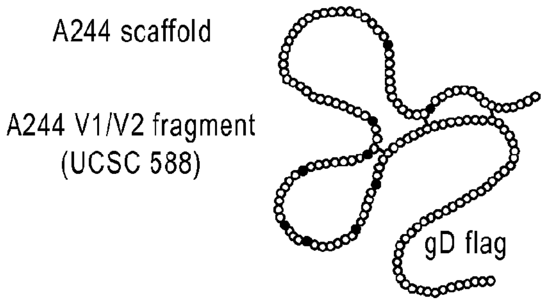

To determine if the inventors could identify scaffolds able to bind PG9-like antibodies, the inventors first tested a series of gp120 fragments from MN-rgp120 recently used to map a panel of mouse MAbs to the V2 domain of MN-rgp120 (9). These fragments were expressed as fusion proteins with the signal sequence and amino-terminal flag epitopes of HSV glycoprotein D (gD). When the inventors tested the fragments produced in normal 293 cells, PG9 was unable to bind to any of the fragments. However when the fragments were produced in GnTI-cells, the inventors found three fragments (7-15, 4-27, and 1-3) that bound PG9 (FIG. 2A). The smallest binding fragment, 1-3, was 265 amino acids in length and included the V1-C3 domains. Thus while production in GnTI-cells improved the binding of gp120 fragments to MN-rgp120, the smallest fragment was far larger than would be ideal for an immunogenic scaffold. To try to find a smaller fragment, the inventors tested a comparable series of fragments from A244-rgp120. The inventors found a 106 amino acid fragment of A244-rgp120 (FIG. 2C) that encompassed the entire V1/V2 domain, that exhibited weak binding to PG9 when expressed in normal 293 cells (data not shown) and high affinity binding when expressed in GnTI-293 cells (FIG. 2B). To further investigate the properties of this fragment, which contained 9 PNGS, the inventors measured binding to three additional PG9-like antibodies: CH01, CH03, and PG16 (3, 8, 15). The inventors found that CH01 and CH03 also bound well to the A244-V1/V2 scaffold when expressed in GnTI-cells but not 293 cells. However, PG16 did not bind to the scaffold regardless of cell type, confirming that this antibody recognized an epitope that included sequences outside of the V2 domain (8, 16). The discovery of the A244-V1/V2 scaffold is an important development because it provides an immunogen with the potential to elicit PG9-like antibodies.

Figure 1C:
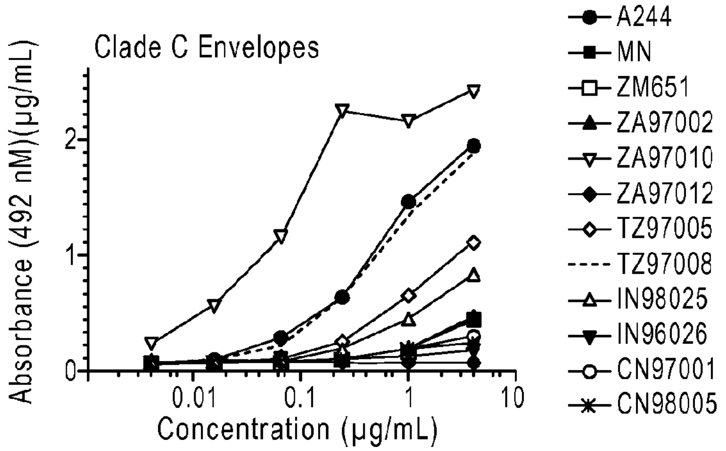

Encouraged by the success of these studies, the inventors attempted to produce V1/V2 scaffolds from other proteins as well. The next scaffold the inventors tried was one made from the CF01_AE TH023 Env that was contained in the vCP1521 pox virus vector used in the RV144 trial. Interestingly, the inventors found that this scaffold exhibited good binding to the PG9 MAb when expressed in GnTI-cells, but little or no binding to the CH01, CH03, or PGT145 MAbs (data not shown). This result confirmed reports suggesting that the PG9, CH01 and CH03 MAbs bind to non-identical overlapping epitopes (8). Our present work involves identifying scaffolds from other clades that the inventors can use for the sequential immunization studies described below. The inventors first screen envelope proteins produced in normal 293 cells for binding to PG9 as observed with A244-rgp120, and then use the best of these to make V1/V2 scaffolds that the inventors express in GnTI-293 cells. Results from a study where the inventors screened Env proteins from a panel of clade C viruses produced in our lab (13) are shown in FIG. 1(C). Based on these results, the Env gene from the ZA97010 isolate appears to have the potential for the production of a V1/V2 scaffold. The inventors have also screened a number of clade B Envs, and have identified several that bind PG9.

Characterization of the Structure of V1/V2 Scaffolds.

Figures 3, 6C:
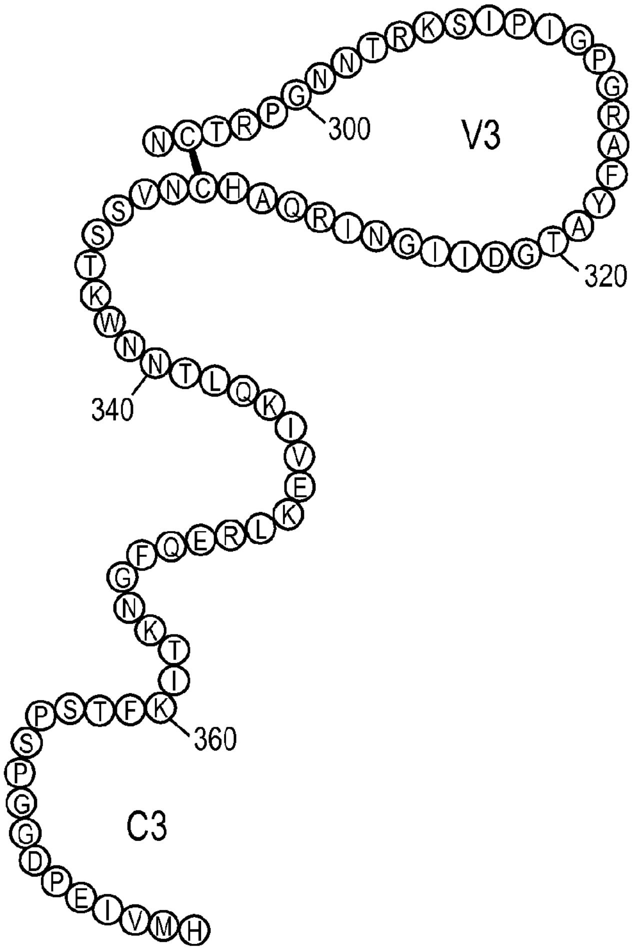
Figures 4, 6C:
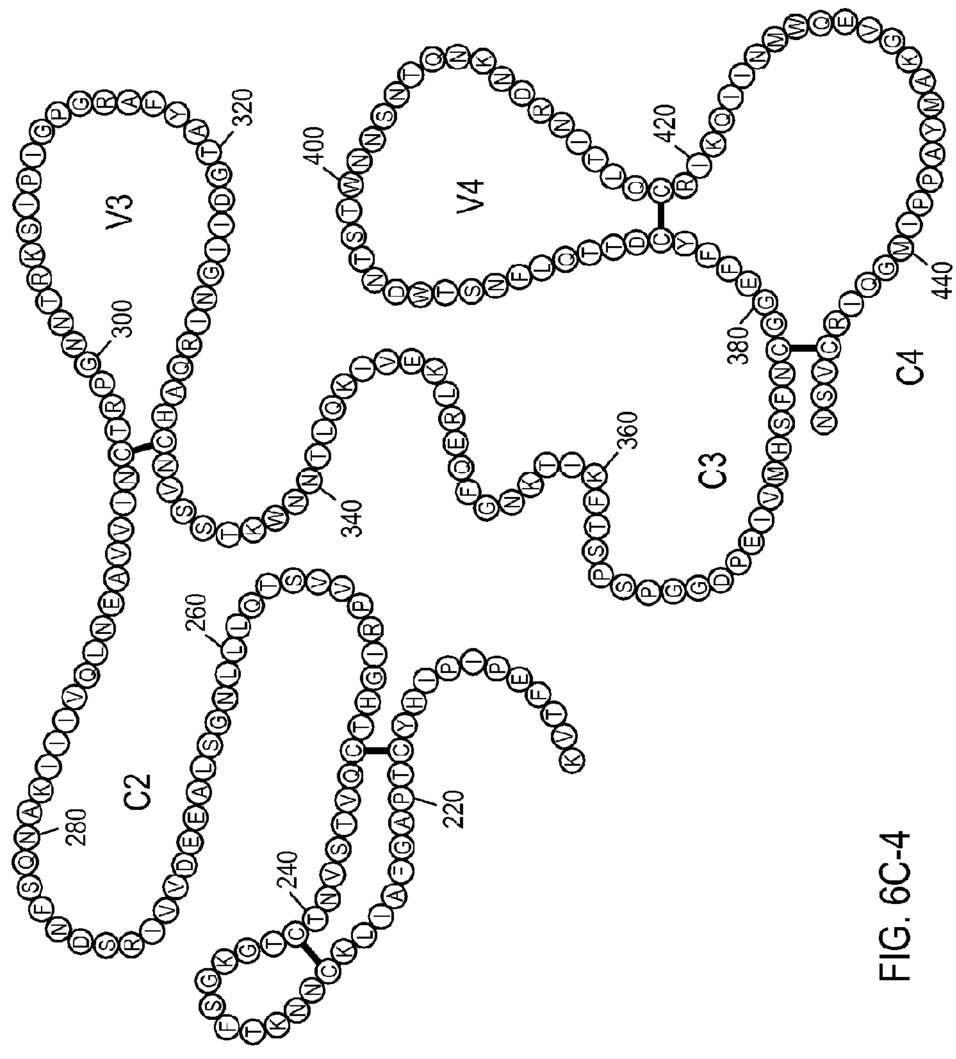
Figures 5, 6C:
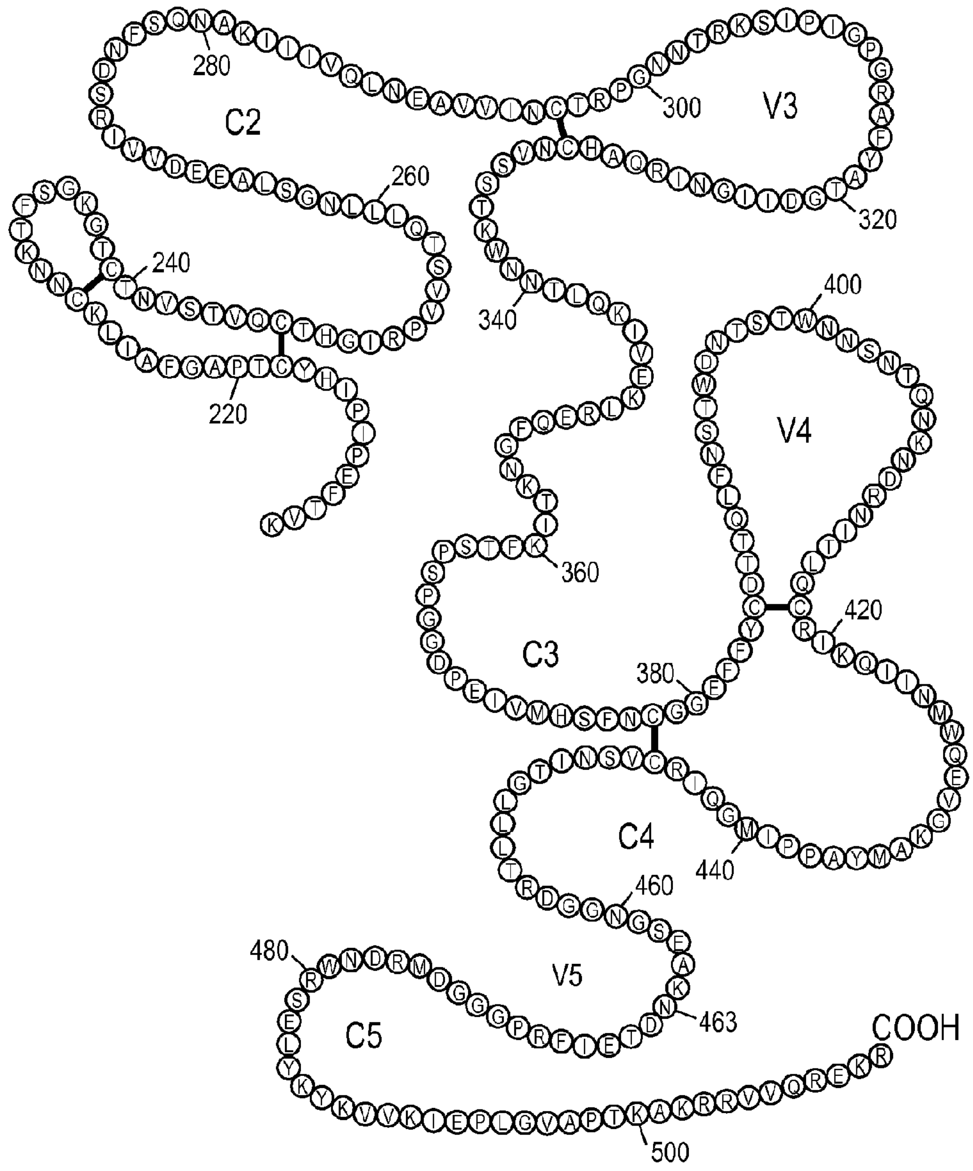

The inventors next wanted to characterize the structure of the A244-V1/V2 scaffold. The inventors first examined the size of the scaffolds produced in normal and GnTI-293 cells by polyacrylamide gel electrophoresis (PAGE). The results of these studies are shown in FIG. 3A. As expected, the V1/V2 scaffold produced in normal 293 cells ran as a diffuse smear of 38-55 kDa. However, the inventors were surprised to see that the A244-V1/V2 scaffold produced in GnTI-cells ran as 3 discrete bands of approximately 38-42 kDa. To investigate this further, the inventors treated the A244-V1/V2 scaffold with PNGase to remove all of the N-linked carbohydrate, or with endoglycosidase H (Endo-H) specific for the high mannose carbohydrate. Treatment with PNGase resulted in a single band of 14 kDa, whereas treatment with Endo-H resulted in a single band of approximately 17 kDa. These results demonstrated that the scaffold was highly glycosylated, and that the differences among the 3 different bands seen in the scaffold produced in GnTI-cells was due to the amount of carbohydrate attached. The extensive difference in size of the glycoprotein scaffold before and after treatment with Endo H was understandable, in view of the fact that there are 9 PNGS (predicted N-linked glycosylation sites) within the 83 amino acid V1/V2 fragment of A244-rgp120. Our results suggested that the variation the inventors observed is likely to be attributable to differences in the usage of particular PNGS. At this point the inventors don't know whether PG9 binds equally to all 3 bands, but immunoprecipitation studies are planned to resolve this issue. In addition, mass spectroscopy studies are in progress to determine whether all of the PNGS sites are utilized.

Because the V1/V2 domain is a 4-stranded anti-parallel β-sheet, this fragment should have a distinctive absorbance profile when measured by circular dichroism (CD). The results of these studies are shown in FIG. 3B. The inventors observed an absorbance pattern at 218 nM clearly indicating the presence of the β-sheet structure. When the inventors measured the absorbance of the same protein that had been reduced and carboxymethylated to destroy the tertiary structure, the pattern changed to that characteristic of a random coil (4). Thus circular dichroism provides a convenient method to verify that the β-sheet structure was preserved in the A244-V1/V2 fragment.

The Mechanism Responsible for the Incorporation of Mannose-5 Glycans at the PG9 Epitope and Mannose-9 at the PGT128 Epitopes.

The discovery of glycan-dependent epitopes in gp120 was intriguing, and the inventors wanted to investigate the mechanism by which HIV-1 is able to selectively incorporate intermediates in the N-linked glycosylation pathway (e.g. mannose-5 and mannose-9) at specific epitopes recognized by the PG9 and PGT128/2G12 MAbs. Several groups have suggested that glycosylation sites are occluded from glycan processing enzymes during the process of gp160 timer formation, leading to incomplete glycosylation at selected sites (5, 6). However, this could not explain the fact that monomeric A244-rgp120 appeared to possess the glycans required for PG9 binding when expressed in normal 293 cells, while gp120 from the MN strain was unable to bind PG9. To account for this phenomenon, the inventors compared the sequences and structural features of MN-rgp120 with A244-rgp120. The inventors noticed that the structure on MN-rgp120 differed from A244 gp120 in the number of glycosylation sites in the V3 stem region where MN-rgp120 possessed 2 PNGS and A244-rgp120 possessed 4 PNGS (FIG. 4A).

Figure 4C:
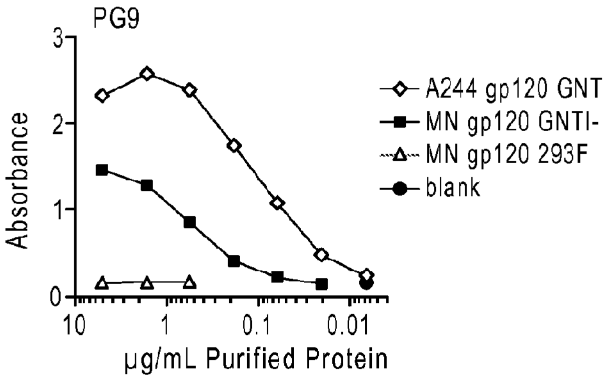
Figure 4D:
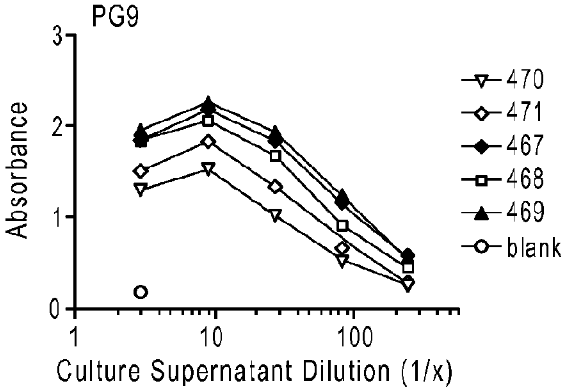
Figure 4E:
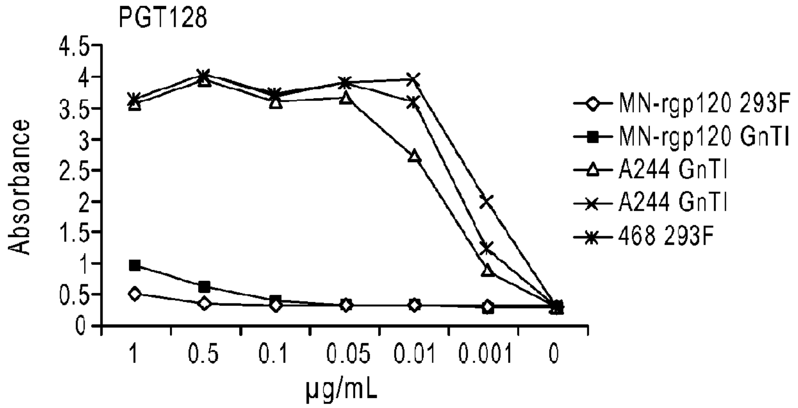

To determine whether the presence of glycosylation sites in the V3 stem might affect the type of glycosylation at the PG9 epitope in the V1/V2 domain, the inventors carried out site-directed mutagenesis to incorporate PNGS (predicted N-linked glycosylation sites) present in the V3 stem of A244-rgp120 into the structure of MN-rgp120 that lacked these sites (FIG. 4A). Astonishingly, the inventors found that addition of two or three PNGS sites at positions 289, 301, and either 332 or 334 resulted in proteins (UCSC 467, 468, and 469) produced in normal 293 cells that were now able to bind to PG9 (FIG. 4B-C). Additionally, the insertion of these glycosylation sites also resulted in the ability of these MN-gp120 glycosylation mutants to bind to the potent PGT128 MAb (FIG. 4D) that requires mannose-9 at positions 301 and 332. Thus, when glycosylation sites are present in the V3 stem (as in the A244-rgp120 or the UCSC 467, 468, and 469 proteins), positions 156 and 160 are sterically protected and inaccessible to glycoprotein processing enzymes, resulting in glycan structures limited to mannose-5 forms.

Previous studies have reported that incomplete glycosylation can result from steric hindrance either by the polypeptide chain or by dense clusters of N-glycans (14). It is likely that both types of interactions result in the incorporation of the glycosylation pathway intermediates required for the binding of the PG9 and PGT128 MAbs. These results suggest that the glycan shield, thought to have evolved in HIV-1 to prevent the binding of neutralizing antibodies, also prevents access by carbohydrate processing enzymes.
Thus PNGS (predicted N-linked glycosylation sites) sometimes interfere with each other, resulting in the incorporation of intermediate structures (e.g. mannose-5 and mannose-9). The development of the monomeric MN-rgp120 glycosylation mutants described above, able to bind two of the most potently neutralizing MAbs described to date (PG9 and PGT128), represents a major advance that should be particularly useful in the development of an improved gp120 subunit vaccine.

Further recent data show that fragments of gp120 from the 108060 isolate of HIV-1 are able to bind the PGT128 MAb that recognizes a mannose 9 dependent glycan epitope in the stem of the V2 domain when the fragments are grown in the presence of kefunensine. PGT128 is the most potent neutralizing monoclonal antibody ever discovered. Kefunensine is a drug that limits N linked glycosylatin to the mannose 9 form.

In one embodiment a subject would be immunized with monomeric gp120s possessing both the PG9 and PGT128 epitopes as with the MN gp120 glycosylation mutant (UCSC468) that the inventors described followed by boosting with a V1/V2 fragment that binds PG9 and a V3 fragment that binds PGT128.

Figure 5:
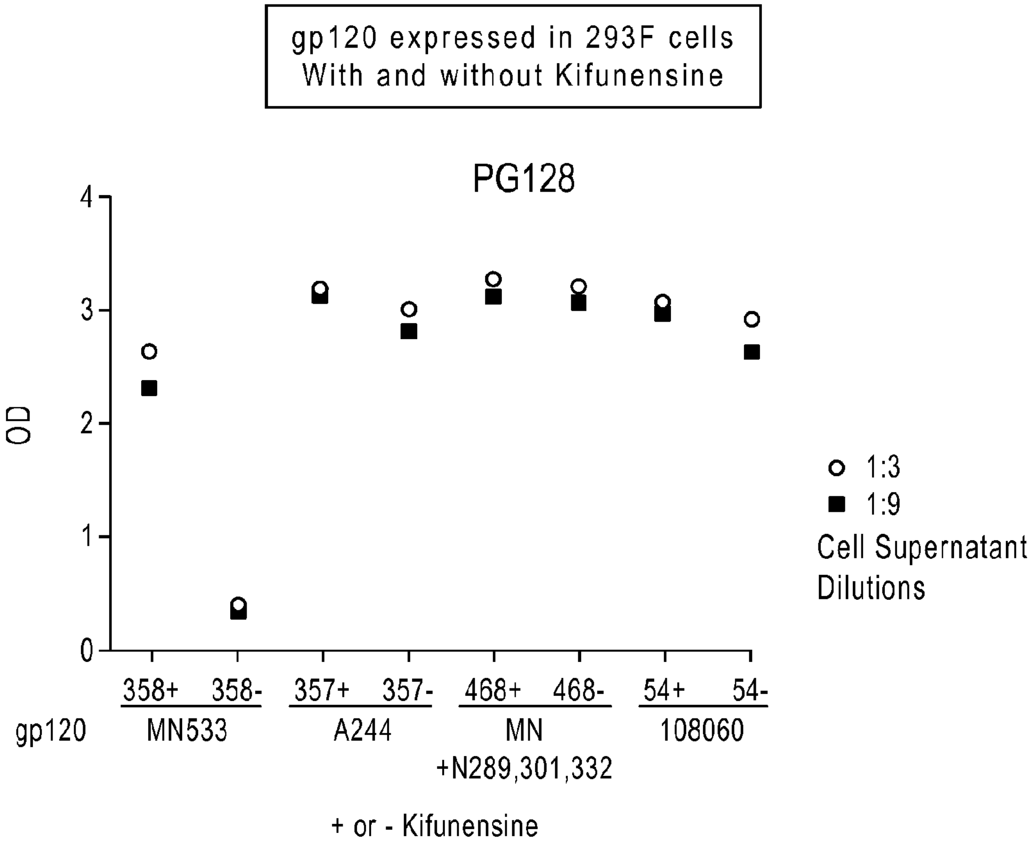
FIG. 5 GP120 expressed in 293F cells with and without Kifunensine.
Figures 6, 6C:
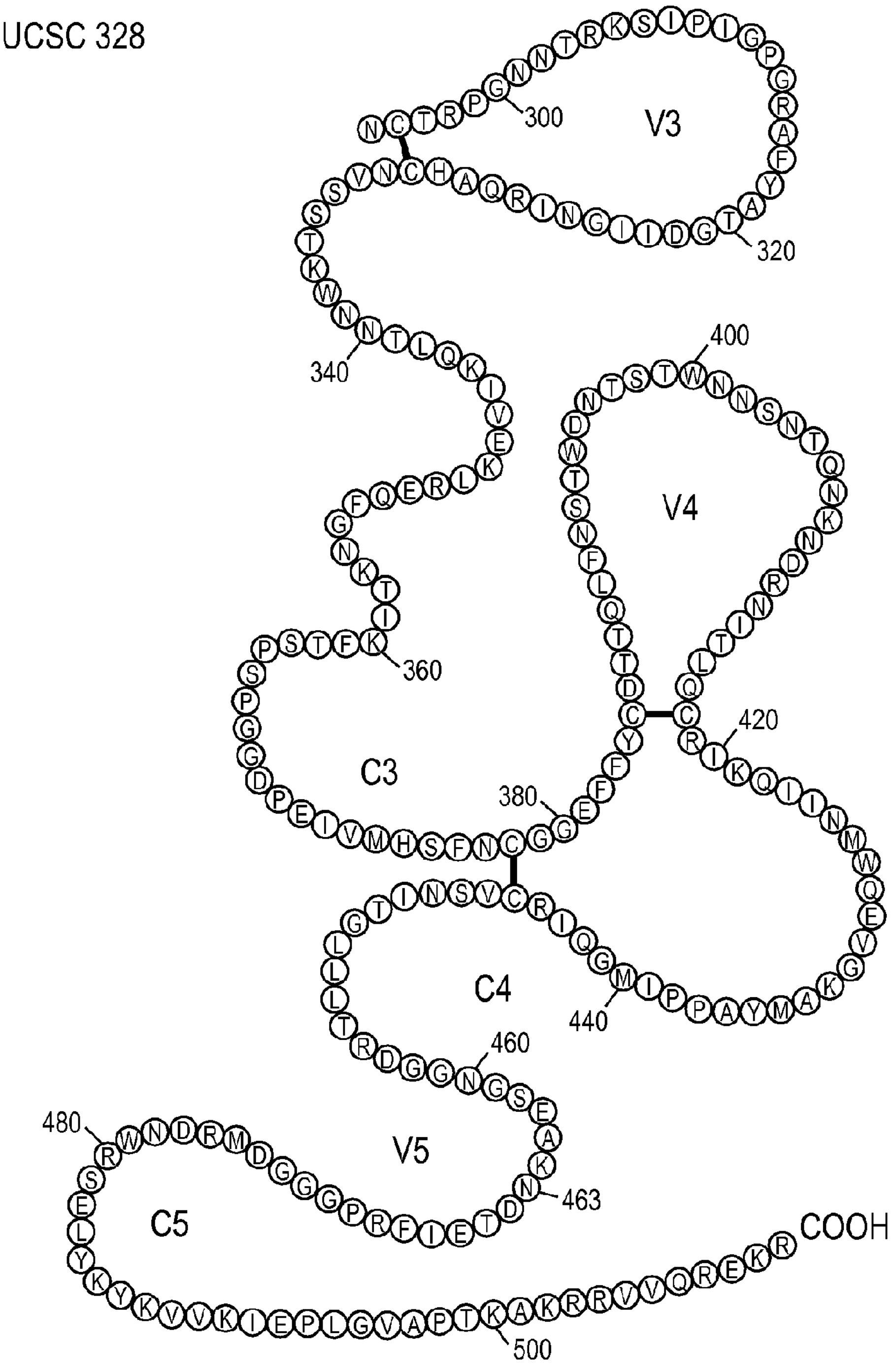
Figure 7:
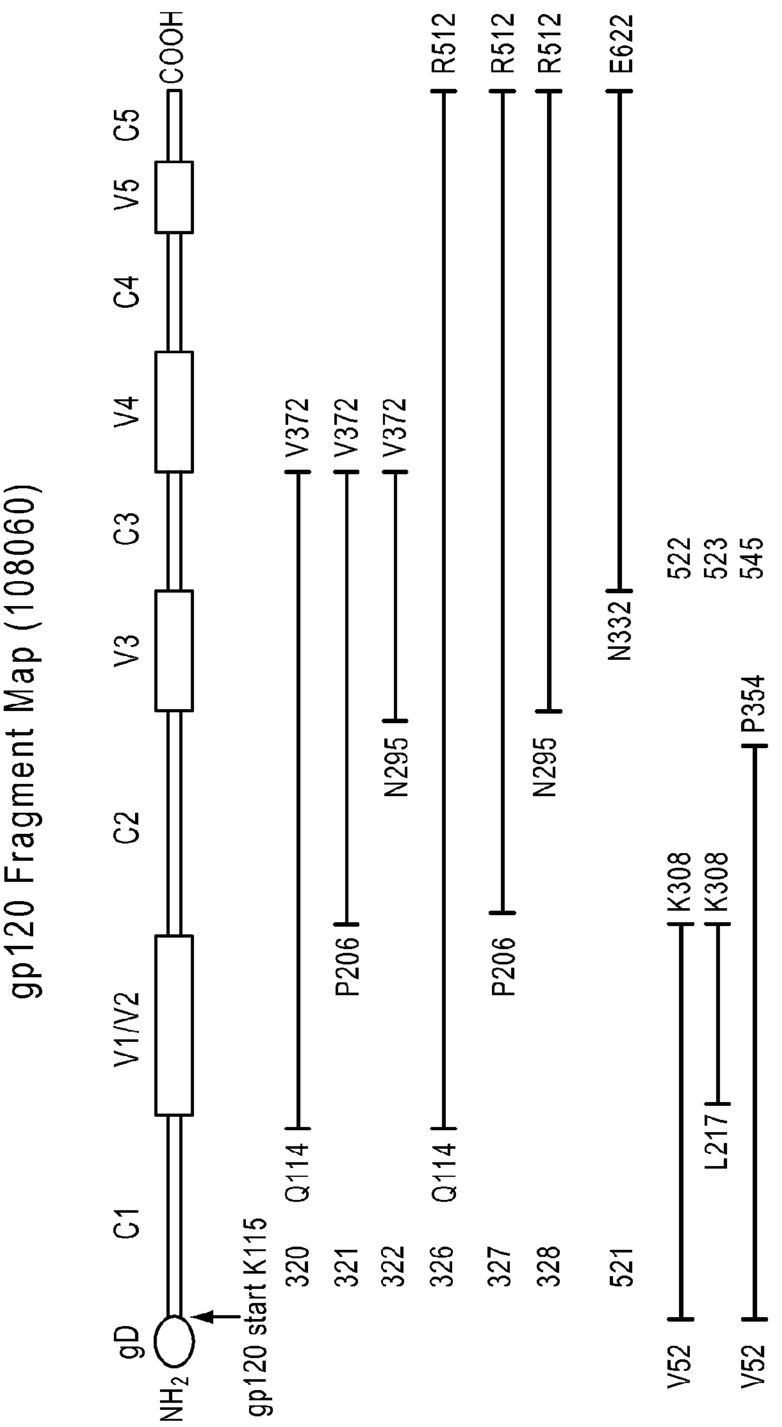
FIG. 7 GP120 fragment map.

The V1/V2 fragment can be A244-V1/V2 produced in GNTI-cells and the V3 fragment can be one of several produced from 108060 envelope protein grown in cells treated with kefunensine. This data shows that use of multiple fragments provides neutralizing monoclonal antibodies. See FIGS. 5, 6, and 7.

Figure 8:
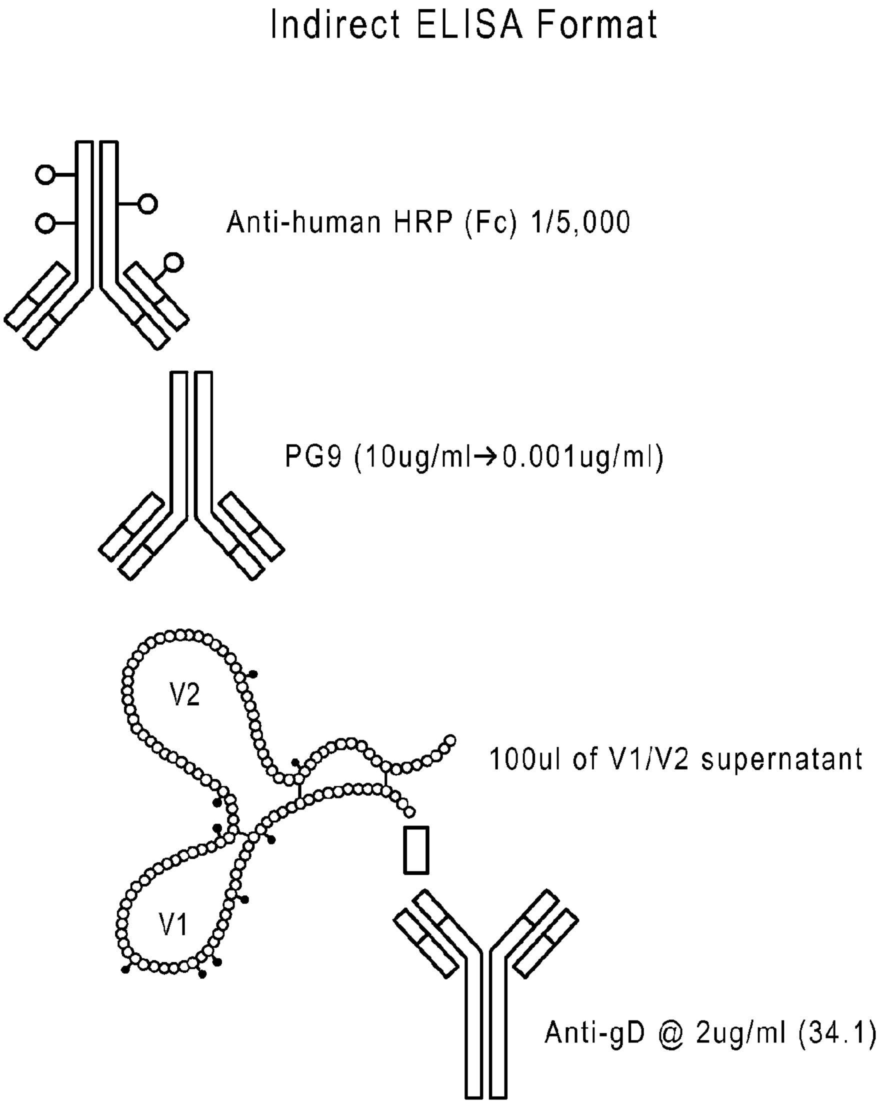
FIG. 8 PG9 binding to V1/V2 scaffolds—Indirect ELISA format.
Figure 9A:
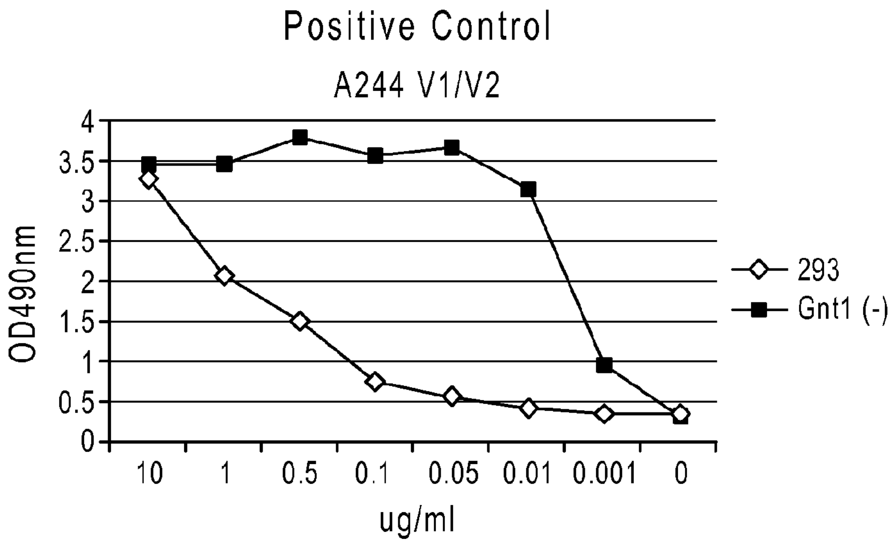
FIGS. 9A-9B PG9 binding to V1/V2 scaffolds—Clade B and control.
Figure 9B:
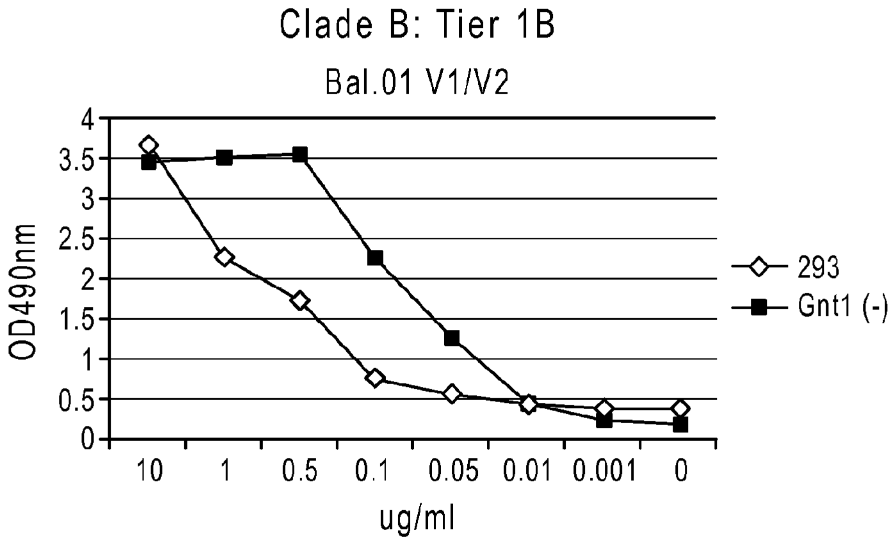
Figure 10A:
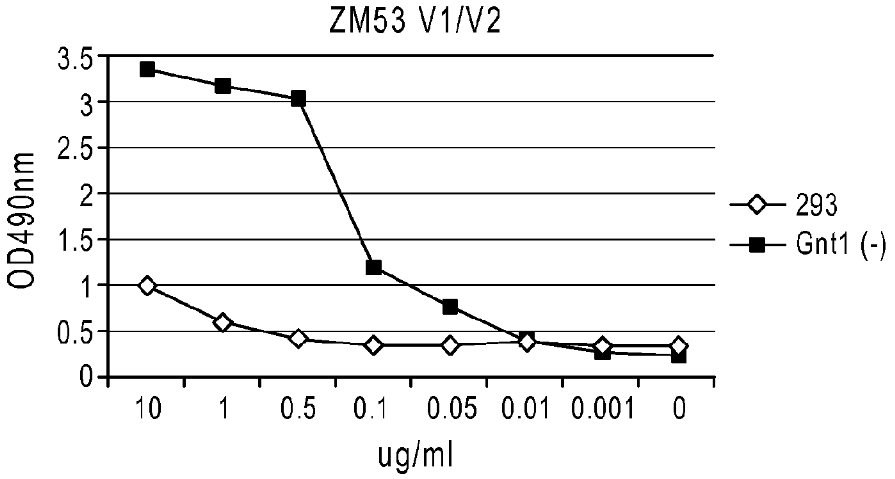
FIGS. 10A-10D PG9 binding to V1/V2 scaffolds—Clade C.
Figure 10B:
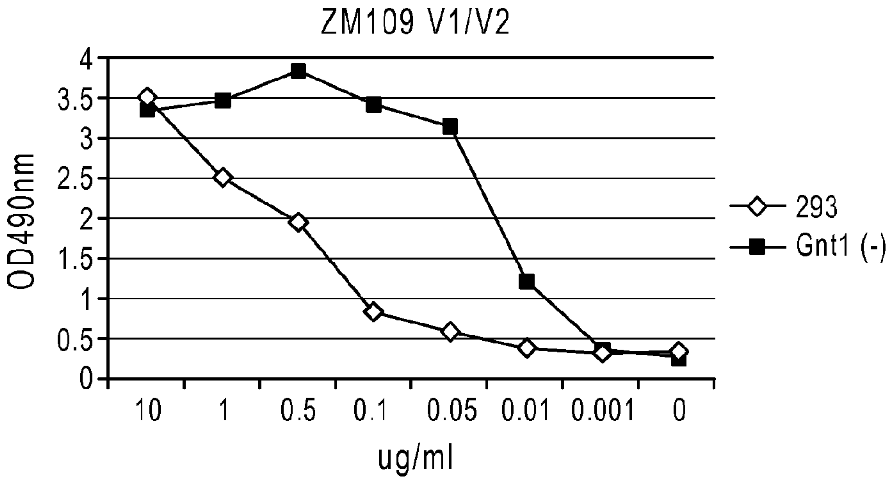
Figure 10C:
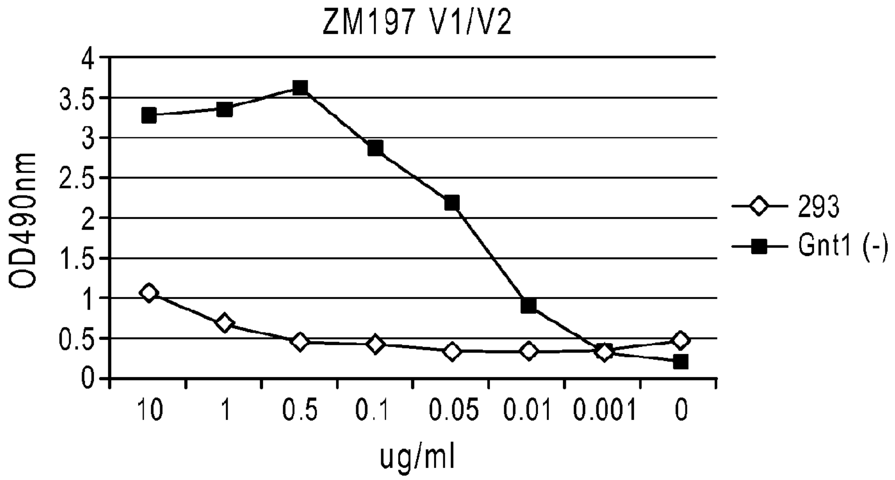
Figure 10D:
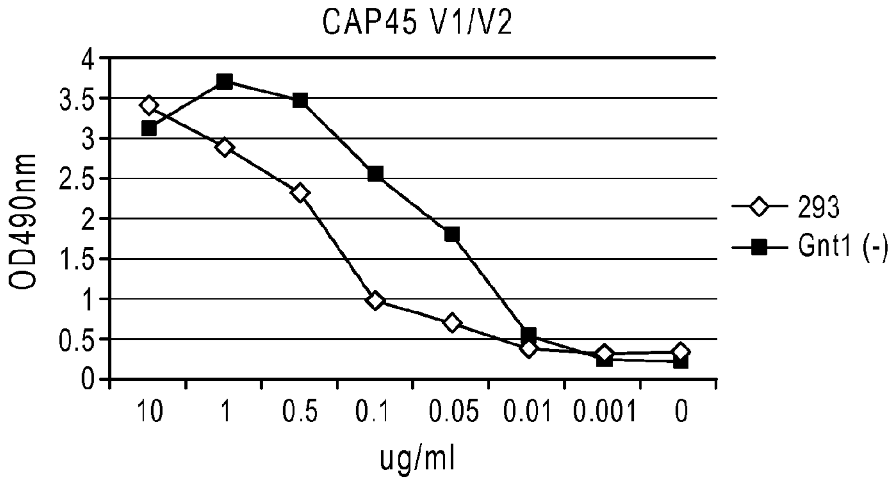
Figure 14A:
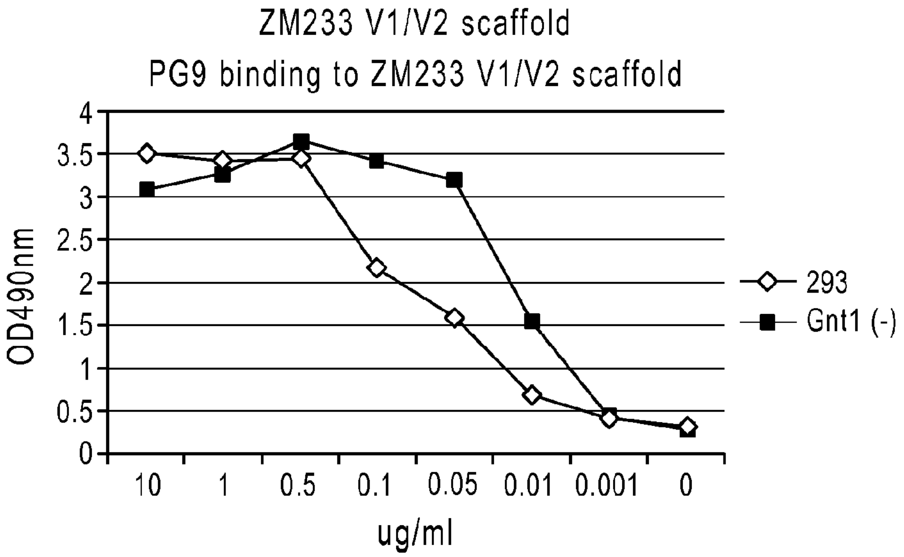
FIGS. 14A-14F are graphs showing ELISA Data of PG9 binding to V1/V2 scaffolds produced in 293 Freestyle™ cells and 293-GnT1-cells. This date relates to the specific, novel, synthetic sequences of FIGS. 12*a-e* and 13*a-f.*
Figure 14B:
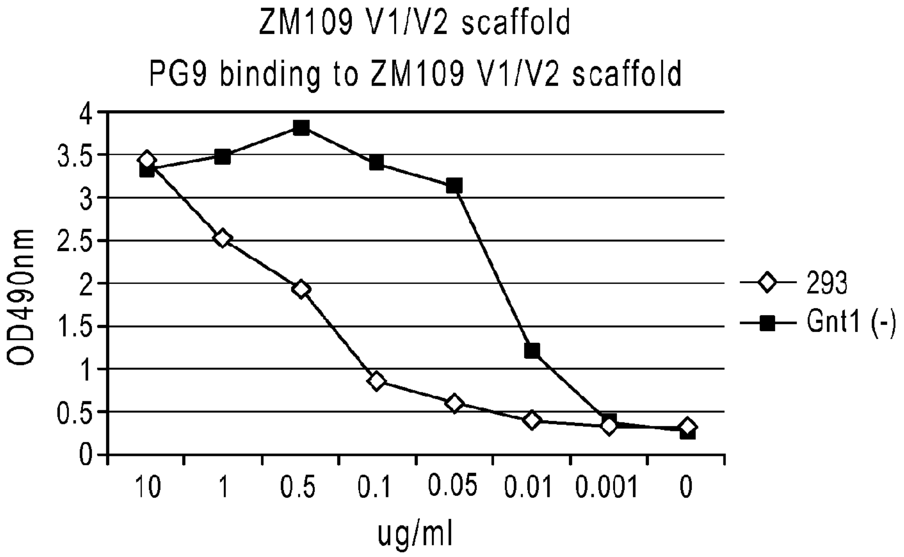
Figure 14C:
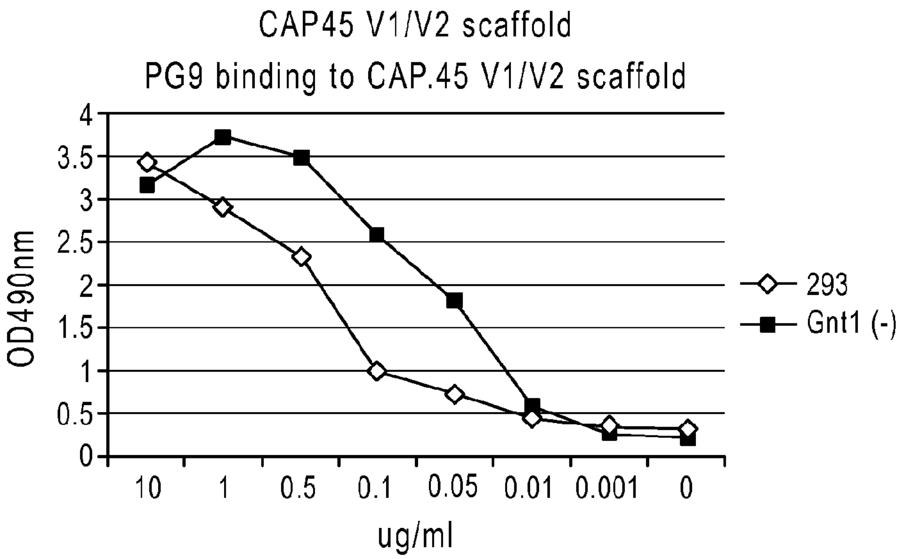
Figure 14D:
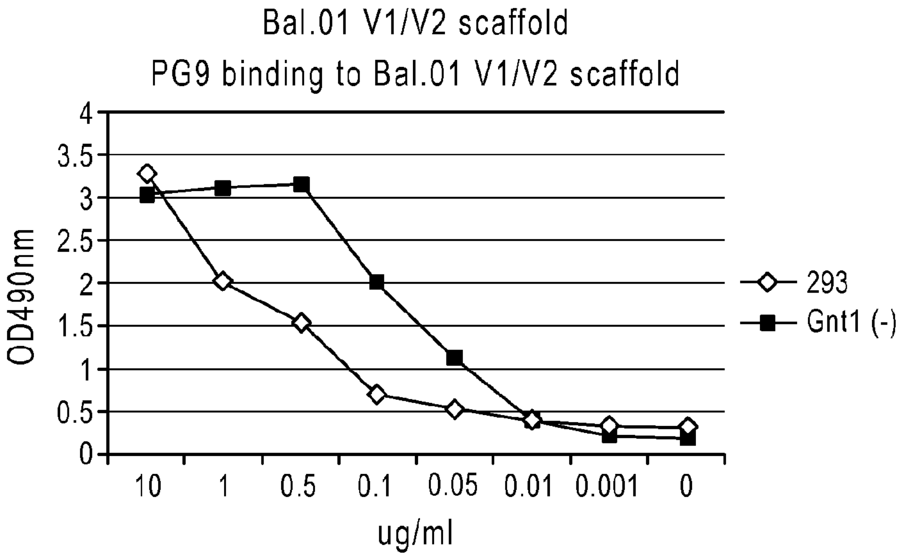
Figure 14E:
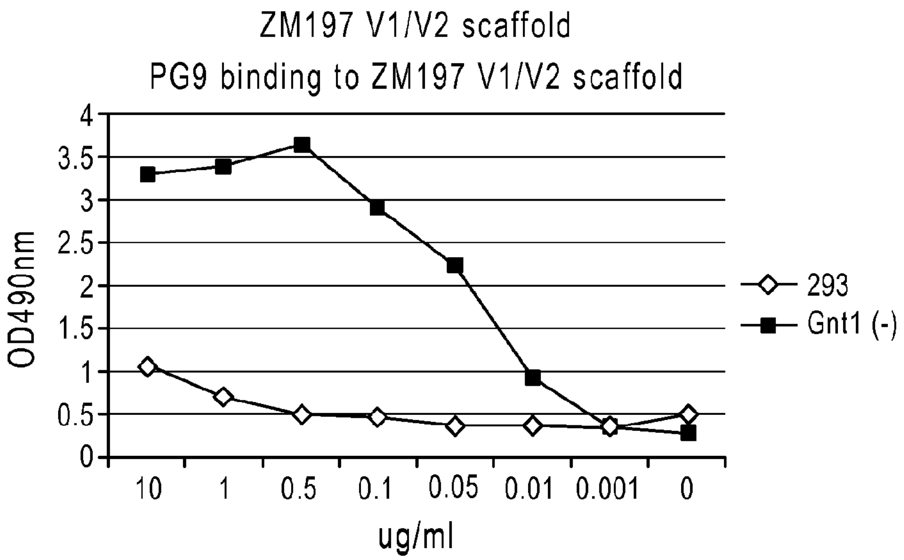
Figure 14F:
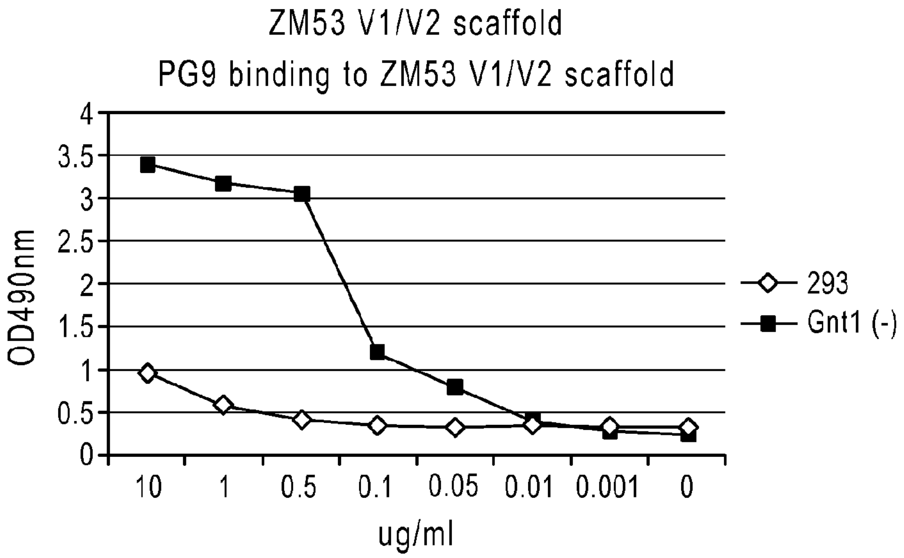

Additional data shows that V1/V2 scaffolds can be made from viruses of other strains and other clades when grown in GNTI-cells. However the binding of PG9 to these appears weaker than to the A244-V1/V2 fragment. Therefore the inventors have made scaffolds from a total of 7 different envelope proteins A244, TH023, BAL, CAP45, ZM109, ZM197, and ZM53. See FIGS. 8, 9 and 10 that show PG9 binding to V1/V2 scaffolds.

Sequences of Scaffold Proteins.

FIG. 11 shows the actual sequence of the two A244 V1/V2 scaffolds that give good binding to the PG9 MAb. The UCSC 588 construct possesses the gD signal sequence (amino-terminal flag epitopes of HSV glycoprotein D) and flag epitope fused to the V1/V2 domain. The UCSC 596 construct lacks the gD flag and has a his tag at the C-terminus. It also has a small 11 amino acid sequence from the mature N-terminus of gp120 inserted between the end of the gD signal sequence and the beginning of the V1/V2 sequence. This sequence represents a consensus sequence from the N-termnus of viruses from the CRF01_AE clade of HIV-1 and was designed to be cleaved at the normal signal peptidase cleavage site. See FIG. 11.

Further Synthetic Engineered Scaffold Proteins

The inventors further engineered synthetic scaffold proteins. These V1/V2 domain scaffolds were all expressed as fusion proteins with the signal sequence and 27 amino acid flag epitope of herpes simplex virus glycoprotein D. In addition to the flag epitope the engineered proteins posess a 3 amino acid linker (LLE).

In most cases the V1/V2 sequence begins with VPL. Experimental data show that these fragments are all able to bind PG9 when grown in GnTI-cells, but bind PG9 poorly when grown in normal 293 cells. However, the ZM233 fragment appears to be unique in that there is good binding to PG9 when this scaffold is produced in normal 293 cells. This characteristic will provide a big advantage in manufacturing since the protein can be produced in some normal cell lines acceptable for the production of human pharmaceuticals.

These synthetic fragments have been successfully expressed using signal sequences from human tissue plasminogen activator and ICAM-1.

Methods for Creating Synthetic Engineered Scaffold Proteins gp160

Plasmid DNA is available through the AIDS Reagent program. ZM233 (Catalog #1131; Accession #DQ388517); ZM109 (Catalog #11314; AY424138); CAP45 (Catalog #11316; Accession #DQ435682); Ba1.01 (Catalog #11445; Accession #DQ318210); ZM53 (Catalog #11313; Accession #AY423984); ZM197 (Catalog #11309; Accession #DQ388515)

Construction of V1/V2 Fragments:

The V1/V2 fragments were PCR amplified from gp160's using primers containing Kpn1 and Not1 restriction sites. The fragments were digested with the corresponding restriction enzymes and ligated into an expression vector (pRK) containing the HSV signal sequence, HSV gD "tag" (amino-terminal flag epitopes of HSV glycoprotein D), and a short peptide linker, LLEVPL, that is used to separate the "tag" from the start of the V1/V2 fragment. The fragments start at amino acid 117 (HXB2 numbering) and end at amino acid 207; a stop codon was placed at position 208. All fragments contain 3 disulfide bonds.

Expression

The V1/V2 fragments were expressed in 293F™ cells (Invitrogen: #R790-07) or 293-GnT1-cells (ATCC: #CRL-3022). Tranfection was done using Polyethylenimine (PEI). Briefly, $1\times10^8$ 293F or GnT1-cells were centrifuged for 10 min. at 1200 rpm. The media was removed and the cells were resuspended in 5 ml of media containing 0.1% pluronic acid; 250 ug of plasmid DNA and 800 ug of PEI was added. After 3 hr incubation at 37° C., the cells were brought up to a final volume of 100 ml. 3-days post-transfection, the cell supernatant was collected, centrifuged, and filtered through a 0.45 um PES membrane.

ELISA Data

Indirect ELISA was used to measure PG9 binding to the V1/V2 fragments. Briefly, Maxisorp ELISA plates (Nunc) were coated with 2 ug/ml of anti-gD antibody (34.1) in PBS overnight at 4° C. The following day the plates were washed 4× with PBS+0.05% Tween-20. The plates were blocked using PBS+1% BSA for 2 hrs at room temperature. Cell supernatant (100 ul) was added for 1 hr. PG9 was added at 10 ug/ml, 1 ug/ml, 0.5 ug/ml, 0.1 ug/ml, 0.05 ug/ml, 0.01 ug/ml, and 0.001 ug/ml. A blank well was used to measure background absorbance. A secondary antibody, anti-human Fc Peroxidase-conjugated, was used to detect PG9. Substrate (OPD) was added for 10 min. and stopped using 3M $H_2SO_4$. All dilutions, (except coating) were done in PBS+ 1% BSA. Wash steps were done after every incubation.

FIGS. 12*a-e* and 13*a-f* show, in FASTA format, Wildtype V1/V2 scaffolds that bind PG9, and synthetic scaffold proteins. These include specific, novel, synthetic sequences (some of which comprise the V1/V2 domain linked to an HSV signal sequence) that show enhanced stability, enhanced binding and a decreased requirement for two glycan binding.

FIGS. 14*a-f* show data for the specific, novel, synthetic sequences of FIGS. 12*a-e* and 13*a-f*. The graphs of FIGS. 14*a-f* show ELISA Data of PG9 binding to V1/V2 scaffolds produced in 293 Freestyle™ cells and 293-GnT1-cells.

Figure 15A:
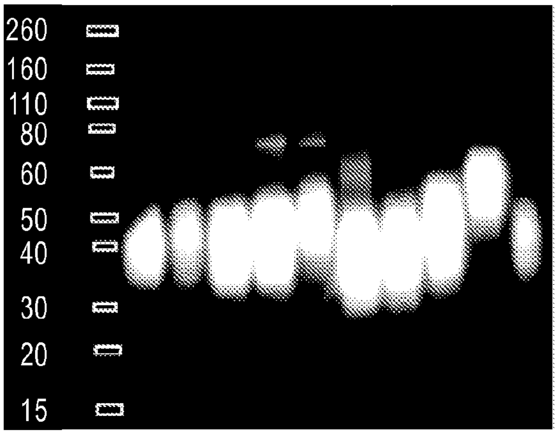
FIG. 15A shows fragments expressed in strain 293F.
Figure 15B:
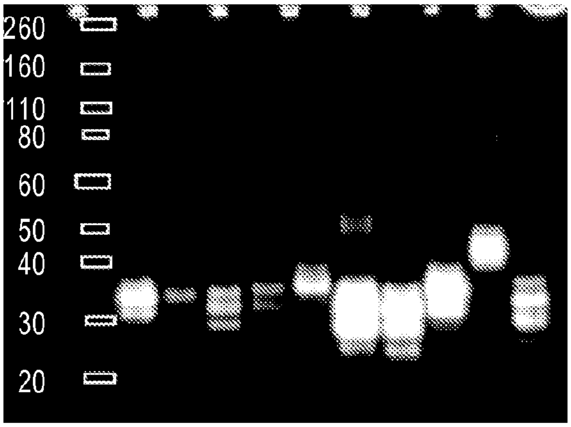
FIG. 15B shows fragments expressed in strain Gnt1(−).

FIG. 15*a* shows fragments expressed in strain 293F and FIG. 15*b* shows fragments expressed in strain Gnt1(−).

Figure 16A:
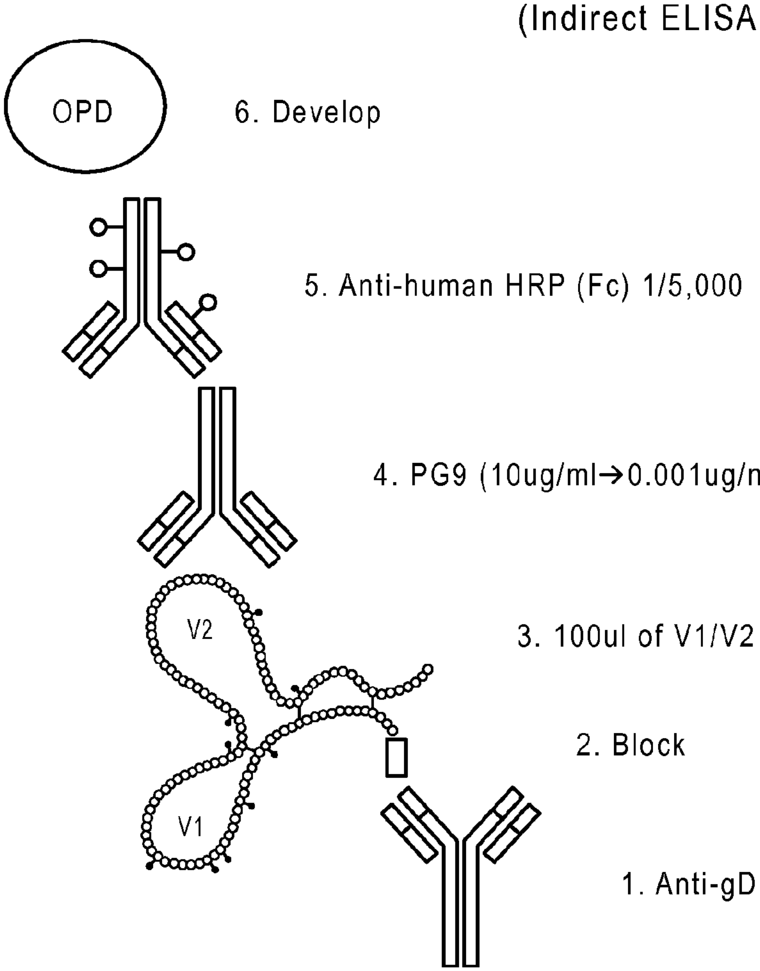
FIGS. 16A-16B is a schematic showing the ELISA method for measuring PG9 binding with the V1/V2 fragments.
Figure 16B:
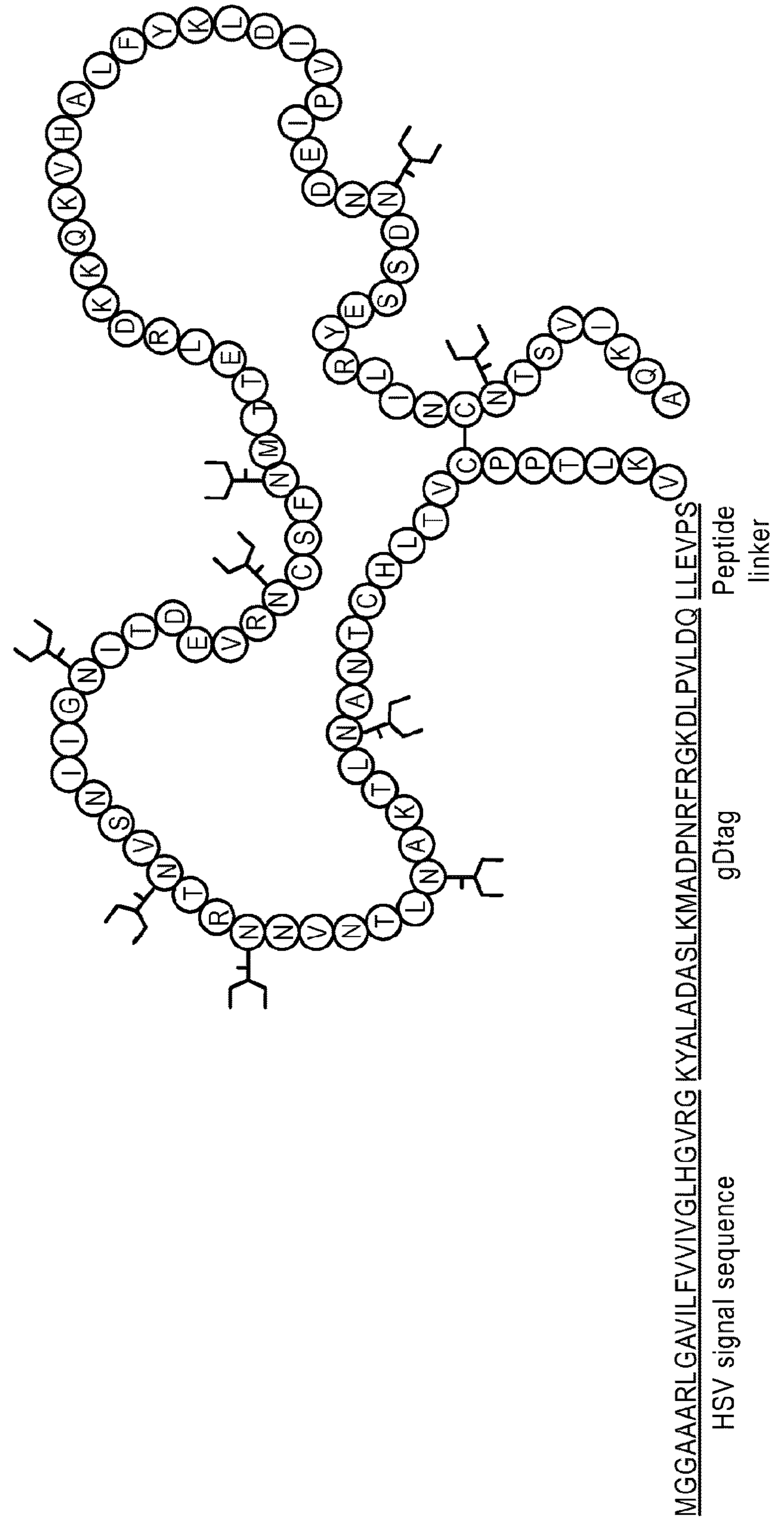

FIG. 16 is a schematic showing the ELISA method for measuring PG9 binding with the V1/V2 fragments. The figure also shows the primary structure of a V1/V2 fragment HSV signal sequence linked to gD tag linked to a Peptide linker. Antibodies bound at their Fc portions at various sites along the peptide are also shown.

CONCLUSION

An important conclusion from this work is that the inventors have discovered that almost any monomeric gp120 will bind to PG9 provided it has the glycosylation sites at positions 156 and 160 and the right amino acids in the area around amino acids 166-173. The inventors have data from several other isolates and novel synthetic constructs showing this to be the case. The present consensus among HIV scientists is that gp120 binds better to trimers because of quaternaty interactions. The inventors have shown this is incorrect—almost any gp120 will bind if its produced in GNT1(−) cells.

Our data suggests that PG9 binds better to trimers because the formation of trimers inside the cell shields positions 156 and 160 from interactions with glycoprocessing enzymes resulting in incomplete glycosylation at these positions. Most monomeric proteins are not shileded from these enzymes and hence acquire the fully mature complex type of carbohdrate that is not recognized by PG9. Thus the incomplete glycosylation resulting from trimerization accounts for the preferential binding of PG9 to trimers and not the presence of an epitope dependent on quaternary interactions.

REFERENCES

1. Berman, P. W. 1998. Development of bivalent rgp120 vaccines to prevent HIV type 1 infection. AIDS Res Hum Retroviruses 14 Suppl 3:S277-89.
2. Berman, P. W., W. Huang, L. Riddle, A. M. Gray, T. Wrin, J. Vennari, A. Johnson, M. Klaussen, H. Prashad, C. Kohne, C. deWit, and T. J. Gregory. 1999. Development of bivalent (B/E) vaccines able to neutralize CCR5-dependent viruses from the United States and Thailand. Virology 265:1-9.
3. Bonsignori, M., K. K. Hwang, X. Chen, C. Y. Tsao, L. Morris, E. Gray, D. J. Marshall, J. A. Crump, S. H. Kapiga, N. E. Sam, F. Sinangil, M. Pancera, Y. Yongping, B. Zhang, J. Zhu, P. D. Kwong, S. O'Dell, J. R. Mascola, L. Wu, G. J. Nabel, S. Phogat, M. S. Seaman, J. F. Whitesides, M. A. Moody, G. Kelsoe, X. Yang, J. Sodroski, G. M. Shaw, D. C. Montefiori, T. B. Kepler, G. D. Tomaras, S. M. Alam, H. X. Liao, and B. F. Haynes. 2011. Analysis of a Clonal Lineage of HIV-1 Envelope V2/V3 Conformational Epitope-Specific Broadly Neutralizing Antibodies and Their Inferred Unmutated Common Ancestors. J Virol 85:9998-10009.
4. Kelly, S. M., T. J. Jess, and N. C. Price. 2005. How to study proteins by circular dichroism. Biochim Biophys Acta 1751:119-39.
5. Kong, L., J.-P. Julien, D. Calarese, C. N. Scanlan, H.-K. Lee, P. Rudd, C.-H. Wong, R. A. Dwek, D. R. Burton, and I. A. Wilson. 2012. Toward a Carbohydrate-Based HIV Vaccine. In A. Klyosov (ed.), Glycobiology and Drug Design, vol. 2012. American Chemical Society, Washington, D.C.
6. Kong, L., and Q. J. Sattentau. 2012. Antigenicity and Immunogenicity in HIV-1 Antibody-Based Vaccine Design. J AIDS Clinic Res S8:003 doi:10.4172/2155-6113.58-003.
7. McCutchan, F. E., P. A. Hegerich, T. P. Brennan, P. Phanuphak, P. Singharaj, A. Jugsudee, P. W. Berman, A. Gray, A. K. Fowler, and D. S. Burke. 1992. Genetic variants of HIV-1 in Thailand. AIDS Res Hum Retroviruses 8:1887-95.
8. McLellan, J. S., M. Pancera, C. Carrico, J. Gorman, J. P. Julien, R. Khayat, R. Louder, R. Pejchal, M. Sastry, K. Dai, S. O'Dell, N. Patel, S. Shahzad-ul-Hussan, Y. Yang, B. Zhang, T. Zhou, J. Zhu, J. C. Boyington, G. Y. Chuang, D. Diwanji, I. Georgiev, Y. D. Kwon, D. Lee, M. K. Louder, S. Moquin, S. D. Schmidt, Z. Y. Yang, M. Bonsignori, J. A. Crump, S. H. Kapiga, N. E. Sam, B. F. Haynes, D. R. Burton, W. C. Koff, L. M. Walker, S. Phogat, R. Wyatt, J. Orwenyo, L. X. Wang, J. Arthos, C. A. Bewley, J. R. Mascola, G. J. Nabel, W. R. Schief, A. B. Ward, I. A. Wilson, and P. D. Kwong. 2011. Structure of HIV-1 gp120 V1/V2 domain with broadly neutralizing antibody PG9. Nature 480:336-43. PMC3406929
9. Nakamura, G. R., D. P. Fonseca, S. M. O'Rourke, A. L. Vollrath, and P. W. Berman. 2012. Monoclonal Antibodies to the V2 Domain of MN-rgp120: Fine Mapping of Epitopes and Inhibition of alpha4beta7 Binding. PLoS One 7:e39045. PMC3374778
10. Pejchal, R., K. J. Doores, L. M. Walker, R. Khayat, P. S. Huang, S. K. Wang, R. L. Stanfield, J. P. Julien, A. Ramos, M. Crispin, R. Depetris, U. Katpally, A. Marozsan, A. Cupo, S. Maloveste, Y. Liu, R. McBride, Y. Ito, R. W. Sanders, C. Ogohara, J. C. Paulson, T. Feizi, C. N. Scanlan, C. H. Wong, J. P. Moore, W. C. Olson, A. B. Ward, P. Poignard, W. R. Schief, D. R. Burton, and I. A. Wilson. 2011. A potent and broad neutralizing antibody recognizes and penetrates the HIV glycan shield. Science 334:1097-103. PMC3280215
11. Pitisuttithum, P., P. Gilbert, M. Gurwith, W. Heyward, M. Martin, F. van Griensven, D. Hu, J. W. Tappero, and K. Choopanya. 2006. Randomized, double-blind, placebo-controlled efficacy trial of a bivalent recombinant glycoprotein 120 HIV-1 vaccine among injection drug users in Bangkok, Thailand. J Infect Dis 194:1661-71.
12. Rerks-Ngarm, S., P. Pitisuttithum, S. Nitayaphan, J. Kaewkungwal, J. Chiu, R. Paris, N. Premsri, C. Namwat, M. de Souza, E. Adams, M. Benenson, S. Gurunathan, J. Tartaglia, J. G. McNeil, D. P. Francis, D. Stablein, D. L. Birx, S. Chunsuttiwat, C. Khamboonruang, P. Thongcharoen, M. L. Robb, N. L. Michael, P. Kunasol, and J. H. Kim. 2009. Vaccination with ALVAC and AIDSVAX to prevent HIV-1 infection in Thailand. N Engl J Med 361:2209-20.

13. Smith, D. H., P. Winters-Digiacinto, M. Mitiku, S. O'Rourke, F. Sinangil, T. Wrin, D. C. Montefiori, and P. W. Berman. 2010. Comparative immunogenicity of HIV-1 clade C envelope proteins for prime/boost studies. PLoS One 5:e12076. PMC2920315

14. Thaysen-Andersen, M., and N. H. Packer. 2012. Site-specific glycoproteomics confirms that protein structure dictates formation of N-glycan type, core fucosylation and branching. Glycobiology doi: 10.1093/glycob/cws110.

15. Walker, L. M., M. Huber, K. J. Doores, E. Falkowska, R. Pejchal, J. P. Julien, S. K. Wang, A. Ramos, P. Y. Chan-Hui, M. Moyle, J. L. Mitcham, P. W. Hammond, O. A. Olsen, P. Phung, S. Fling, C. H. Wong, S. Phogat, T. Wrin, M. D. Simek, G. P. I. Protocol, W. C. Koff, I. A. Wilson, D. R. Burton, and P. Poignard. 2011. Broad neutralization coverage of HIV by multiple highly potent antibodies. Nature 477:466-70.

16. Walker, L. M., S. K. Phogat, P. Y. Chan-Hui, D. Wagner, P. Phung, J. L. Goss, T. Wrin, M. D. Simek, S. Fling, J. L. Mitcham, J. K. Lehrman, F. H. Priddy, O. A. Olsen, S. M. Frey, P. W. Hammond, S. Kaminsky, T. Zamb, M. Moyle, W. C. Koff, P. Poignard, and D. R. Burton. 2009. Broad and potent neutralizing antibodies from an African donor reveal a new HIV-1 vaccine target. Science 326:285-9. PMC3335270

17. Yu, B., J. F. Morales, S. M. O'Rourke, G. P. Tatsuno, and P. W. Berman. 2012. Glycoform and Net Charge Heterogeneity in gp120 Immunogens Used in HIV Vaccine Trials. PLoS One 7:e43903. PMC3425498

The invention claimed is:

1. A method for producing a V1/V2 fragment of a HIV-1 envelope glycoprotein gp120 for use in eliciting broadly neutralizing antibodies, wherein the V1/V2 fragment binds to the broadly neutralizing PG9 monoclonal antibody (MAb), the method comprising:

expressing the V1/V2 fragment in a cell line lacking an N-acetylglucosaminyltransferase I (GnTI) enzyme activity, wherein the V1/V2 fragment comprises mannose-5 glycans and comprises the amino acid sequence as set forth in SEQ ID NO: 16.

2. The method of claim 1, further comprising expressing a HIV-1 envelope glycoprotein, gp120, in a cell line lacking an N-acetylglucosaminyltransferase I (GnTI) enzyme activity and producing a formulation comprising the gp120 and the V1/V2 fragment, wherein mannose-5 glycan is incorporated in the gp120 and the V1/V2 fragment.

3. The method of claim 1, wherein the V1/V2 fragment is expressed as a fusion protein comprising a signal sequence, a tag, and a linker.

4. The method of claim 2, wherein the gp120 is a MN-rgp120 polypeptide comprising an amino acid sequence selected from the group consisting of SEQ ID NO: 3, SEQ ID NO: 4, SEQ ID NO: 5, SEQ ID NO: 6, and SEQ ID NO: 7 wherein said MN-rgp120, when expressed in normal 293 cells, binds to PG9 and PGT128 MAb.

5. The method of claim 4, wherein the MN-rgp120 comprises the amino acid sequence set forth in SEQ ID NO: 3.

6. The method of claim 1, wherein the V1/V2 fragment is expressed as a fusion protein comprising a signal sequence, the 27 N-terminal amino acids of herpes simplex virus glycoprotein D, and a 3 amino acid linker (LLE).

7. The method of claim 2, wherein the gp120 is A244-rgp120.

8. A formulation comprising a V1/V2 fragment of a HIV-1 envelope glycoprotein gp120 wherein the V1/V2 fragment comprises mannose-5 glycans and comprises the amino acid sequence as set forth in SEQ ID NO: 16.

9. The formulation of claim 8, wherein the V1/V2 fragment is conjugated to a signal sequence.

10. The formulation of claim 8, further comprising a HIV-1 envelope glycoprotein, A244-gp120, wherein mannose-5 glycan is incorporated in the A244-gp120.

11. The formulation of claim 8, further comprising a HIV-1 envelope gp120 glycoprotein, wherein the gp120 is MN-rgp120 comprising an amino acid sequence selected from the group consisting of SEQ ID NO: 3, SEQ ID NO: 4, SEQ ID NO: 5, SEQ ID NO: 6, and SEQ ID NO: 7, wherein said MN-rgp120, when expressed in normal 293 cells, binds to PG9 and PGT128 MAb.

12. The formulation of claim 11, wherein the MN-rgp120 comprises the amino acid sequence set forth in SEQ ID NO: 3.

* * * * *

SEQUENCE LISTING

```
<160> NUMBER OF SEQ ID NOS: 21

<210> SEQ ID NO 1
<211> LENGTH: 69
<212> TYPE: PRT
<213> ORGANISM: HIV-1, A244 strain

<400> SEQUENCE: 1

Asn Asn Ala Lys Thr Ile Ile Val His Leu Asn Lys Ser Val Val Ile
1               5                   10                  15

Asn Cys Thr Arg Pro Ser Asn Asn Thr Arg Thr Ser Ile Thr Ile Gly
            20                  25                  30

Pro Gly Gln Val Phe Tyr Arg Thr Gly Asp Ile Ile Gly Asp Ile Arg
        35                  40                  45

Lys Ala Tyr Cys Glu Ile Asn Gly Thr Glu Trp Asn Lys Ala Leu Lys
    50                  55                  60

Gln Val Thr Glu Lys
65


<210> SEQ ID NO 2
<211> LENGTH: 69
<212> TYPE: PRT
<213> ORGANISM: Artificial Sequence
<220> FEATURE:
<223> OTHER INFORMATION: MN-rgp120

<400> SEQUENCE: 2

Asp Asn Ala Lys Thr Ile Ile Val His Leu Lys Glu Ser Val Gln Ile
1               5                   10                  15

Asn Cys Thr Arg Pro Asn Tyr Asn Lys Arg Lys Arg Ile His Ile Gly
            20                  25                  30

Pro Gly Arg Ala Phe Tyr Thr Thr Lys Asn Ile Lys Gly Thr Ile Arg
        35                  40                  45

Gln Ala His Cys Ile Ile Ser Arg Ala Lys Trp Asn Asp Thr Lys Arg
    50                  55                  60

Gln Ile Val Ser Lys
65


<210> SEQ ID NO 3
<211> LENGTH: 69
<212> TYPE: PRT
<213> ORGANISM: Artificial Sequence
<220> FEATURE:
<223> OTHER INFORMATION: mutated MN-rgp120
```

<400> SEQUENCE: 3

Asp Asn Ala Lys Thr Ile Ile Val His Leu Lys Glu Ser Val Gln Ile
1 5 10 15

Asn Cys Thr Arg Pro Asn Tyr Asn Lys Arg Lys Arg Ile His Ile Gly
20 25 30

Pro Gly Arg Ala Phe Tyr Thr Thr Lys Asn Ile Lys Gly Thr Ile Arg
35 40 45

Gln Ala His Cys Asn Ile Ser Arg Ala Lys Trp Asn Asp Thr Lys Arg
50 55 60

Gln Ile Val Ser Lys
65

<210> SEQ ID NO 4
<211> LENGTH: 69
<212> TYPE: PRT
<213> ORGANISM: Artificial Sequence
<220> FEATURE:
<223> OTHER INFORMATION: mutated MN-rgp120

<400> SEQUENCE: 4

Asp Asn Ala Lys Thr Ile Ile Val His Leu Lys Glu Ser Val Gln Ile
1 5 10 15

Asn Cys Thr Arg Pro Asn Tyr Asn Lys Arg Lys Arg Ile His Ile Gly
20 25 30

Pro Gly Arg Ala Phe Tyr Thr Thr Lys Asn Ile Lys Gly Thr Ile Arg
35 40 45

Gln Ala His Cys Ile Ile Asn Arg Thr Lys Trp Asn Asp Thr Lys Arg
50 55 60

Gln Ile Val Ser Lys
65

<210> SEQ ID NO 5
<211> LENGTH: 69
<212> TYPE: PRT
<213> ORGANISM: Artificial Sequence
<220> FEATURE:
<223> OTHER INFORMATION: mutated MN-rgp120

<400> SEQUENCE: 5

Asp Asn Ala Lys Thr Ile Ile Val His Leu Asn Glu Ser Val Gln Ile
1 5 10 15

Asn Cys Thr Arg Pro Asn Asn Asn Thr Arg Lys Arg Ile His Ile Gly
20 25 30

Pro Gly Arg Ala Phe Tyr Thr Thr Lys Asn Ile Lys Gly Thr Ile Arg
35 40 45

Gln Ala His Cys Ile Ile Ser Arg Ala Lys Trp Asn Asp Thr Lys Arg
50 55 60

Gln Ile Val Ser Lys
65

<210> SEQ ID NO 6
<211> LENGTH: 69
<212> TYPE: PRT
<213> ORGANISM: Artificial Sequence
<220> FEATURE:
<223> OTHER INFORMATION: mutated MN-rgp120

<400> SEQUENCE: 6

Asp Asn Ala Lys Thr Ile Ile Val His Leu Asn Glu Ser Val Gln Ile
1 5 10 15

Asn Cys Thr Arg Pro Asn Asn Asn Thr Arg Lys Arg Ile His Ile Gly
20 25 30

Pro Gly Arg Ala Phe Tyr Thr Thr Lys Asn Ile Lys Gly Thr Ile Arg
35 40 45

Gln Ala His Cys Asn Ile Ser Arg Ala Lys Trp Asn Asp Thr Lys Arg
50 55 60

Gln Ile Val Ser Lys
65

<210> SEQ ID NO 7
<211> LENGTH: 69
<212> TYPE: PRT
<213> ORGANISM: Artificial Sequence
<220> FEATURE:
<223> OTHER INFORMATION: mutated MN-rgp120

<400> SEQUENCE: 7

Asp Asn Ala Lys Thr Ile Ile Val His Leu Asn Glu Ser Val Gln Ile
1 5 10 15

Asn Cys Thr Arg Pro Asn Asn Asn Thr Arg Lys Arg Ile His Ile Gly
20 25 30

Pro Gly Arg Ala Phe Tyr Thr Thr Lys Asn Ile Lys Gly Thr Ile Arg
35 40 45

Gln Ala His Cys Ile Ile Asn Arg Thr Lys Trp Asn Asp Thr Lys Arg
50 55 60

Gln Ile Val Ser Lys
65

<210> SEQ ID NO 8
<211> LENGTH: 152
<212> TYPE: PRT
<213> ORGANISM: Artificial Sequence
<220> FEATURE:
<223> OTHER INFORMATION: A244 V1/V2 Scaffold

<400> SEQUENCE: 8

Met Gly Gly Ala Ala Ala Arg Leu Gly Ala Val Ile Leu Phe Val Val
1 5 10 15

Ile Val Gly Leu His Gly Val Arg Gly Lys Tyr Ala Leu Ala Asp Ala
20 25 30

Ser Leu Lys Met Ala Asp Pro Asn Arg Phe Arg Gly Lys Asp Leu Pro
35 40 45

Val Leu Asp Gln Leu Leu Glu Val Pro Ser Val Lys Leu Thr Pro Pro
50 55 60

Cys Val Thr Leu His Cys Thr Asn Ala Asn Leu Thr Lys Ala Asn Leu
65 70 75 80

Thr Asn Val Asn Asn Arg Thr Asn Val Ser Asn Ile Ile Gly Asn Ile
85 90 95

Thr Asp Glu Val Arg Asn Cys Ser Phe Asn Met Thr Thr Glu Leu Arg
100 105 110

Asp Lys Lys Gln Lys Val His Ala Leu Phe Tyr Lys Leu Asp Ile Val
115 120 125

-continued

Pro Ile Glu Asp Asn Asn Asp Ser Ser Glu Tyr Arg Leu Ile Asn Cys
    130                 135                 140

Asn Thr Ser Val Ile Lys Gln Ala
145                 150

<210> SEQ ID NO 9
<211> LENGTH: 142
<212> TYPE: PRT
<213> ORGANISM: Artificial Sequence
<220> FEATURE:
<223> OTHER INFORMATION: A244 V1/V2 Scaffold

<400> SEQUENCE: 9

Met Gly Gly Ala Ala Ala Arg Leu Gly Ala Val Ile Leu Phe Val Val
1               5                   10                  15

Ile Val Gly Leu His Gly Val Arg Gly Thr Asp Asn Leu Trp Val Thr
            20                  25                  30

Val Tyr Tyr Gly Val Pro Ser Val Lys Leu Thr Pro Pro Cys Val Thr
        35                  40                  45

Leu His Cys Thr Asn Ala Asn Leu Thr Lys Ala Asn Leu Thr Asn Val
    50                  55                  60

Asn Asn Arg Thr Asn Val Ser Asn Ile Ile Gly Asn Ile Thr Asp Glu
65                  70                  75                  80

Val Arg Asn Cys Ser Phe Asn Met Thr Thr Glu Leu Arg Asp Lys Lys
                85                  90                  95

Gln Lys Val His Ala Leu Phe Tyr Lys Leu Asp Ile Val Pro Ile Glu
            100                 105                 110

Asp Asn Asn Asp Ser Ser Glu Tyr Arg Leu Ile Asn Cys Asn Thr Ser
        115                 120                 125

Val Ile Lys Gln Ala Ser Gly Arg His His His His His His
    130                 135                 140

<210> SEQ ID NO 10
<211> LENGTH: 426
<212> TYPE: DNA
<213> ORGANISM: Artificial Sequence
<220> FEATURE:
<223> OTHER INFORMATION: ZM233M.PB6 SVPC9 V1/V2 DNA sequence

<400> SEQUENCE: 10
atgggggggg ctgccgccag gttgggggcc gtgattttgt ttgtcgtcat agtgggcctc 60
catggggtcc gcggcaaata tgccttggcg gatgcctctc tcaagatggc cgaccccaat 120
cgatttcgcg gcaaagacct tccggtcctg gaccagctgc tcgaggtacc actaaagcca 180
tgtgtaaagt tgaccccact ctgtgtcact ttggattgta gtacctacaa taatacccac 240
aatattagta aggagatgaa aatttgctct ttcaatatga ccacagaact aagagataag 300
aaacggaaag tgaatgtact tttttataaa cttgatttag tgccacttac caattctagc 360
aatactacca attatagatt aataagttgt aatacttcaa ccataacaca agcctgtcca 420
aagtag 426

<210> SEQ ID NO 11
<211> LENGTH: 435
<212> TYPE: DNA
<213> ORGANISM: Artificial Sequence
<220> FEATURE:
<223> OTHER INFORMATION: ZM109F.PB4 SVPC13 V1/V2 DNA sequence -continued

<400> SEQUENCE: 11

```
atgggggggg ctgccgccag gttgggggcc gtgattttgt ttgtcgtcat agtgggcctc     60
catggggtcc gcggcaaata tgccttggcg gatgcctctc tcaagatggc cgaccccaat    120
cgatttcgcg gcaaagacct tccggtcctg gaccagctgc tcgaggtacc actaaagcca    180
tgtgtaaaat tgaccccact ctgtgtcact ttaaattgta caagtcctgc tgcccacaat    240
gagagcgaga caagagtaaa acattgctct ttcaatataa ccacagatgt aaaagataga    300
aaacagaagg tgaatgcaac tttttatgac cttgatatag taccacttag cagctctgac    360
aactctagca actctagtct gtatagatta ataagttgta atacctcaac cataacacaa    420
gcctgtccaa agtag                                                     435
```

<210> SEQ ID NO 12
<211> LENGTH: 435
<212> TYPE: DNA
<213> ORGANISM: Artificial Sequence
<220> FEATURE:
<223> OTHER INFORMATION: CAP45.2.00.G3 SVPC16 V1/V2 DNA sequence

<400> SEQUENCE: 12

```
atgggggggg ctgccgccag gttgggggcc gtgattttgt ttgtcgtcat agtgggcctc     60
catggggtcc gcggcaaata tgccttggcg gatgcctctc tcaagatggc cgaccccaat    120
cgatttcgcg gcaaagacct tccggtcctg gaccagctgc tcgaggtacc actaaagcca    180
tgtgtaaagt tgaccccact ctgtgtcact ttaaggtgta caaatgctac tattaatggt    240
agcctgacgg aagaagtaaa aaattgctct ttcaatataa ccacagagct aagagataag    300
aaacagaaag cgtatgcact tttttataga cctgatgtag taccacttaa taagaatagc    360
cctagtggga attctagtga gtatatatta ataaattgca atacctcaac cataacacaa    420
gcctgtccaa agtag                                                     435
```

<210> SEQ ID NO 13
<211> LENGTH: 462
<212> TYPE: DNA
<213> ORGANISM: Artificial Sequence
<220> FEATURE:
<223> OTHER INFORMATION: Bal.01 V1/V2 DNA sequence

<400> SEQUENCE: 13

```
atgggggggg ctgccgccag gttgggggcc gtgattttgt ttgtcgtcat agtgggcctc     60
catggggtcc gcggcaaata tgccttggcg gatgcctctc tcaagatggc cgaccccaat    120
cgatttcgcg gcaaagacct tccggtcctg gaccagctgc tcgaggtacc actaaagcca    180
tgtgtaaaat taaccccact ctgtgttact ttaaattgca ctgatttgag gaatgctact    240
agtaggaatg ttactaatac cactagtagt agcaggggaa tggtgggggg aggagaaatg    300
aaaaattgct ctttcaatat caccacaggc ataagaggta aggtgcagaa agaatatgca    360
ctttttttatg aacttgatat agtaccaata gataataaaa ttgatagata taggttgata    420
agttgtaaca cctcagtcat tacacaggcc tgtccaaagt ag                       462
```

<210> SEQ ID NO 14
<211> LENGTH: 513
<212> TYPE: DNA
<213> ORGANISM: Artificial Sequence
<220> FEATURE:
<223> OTHER INFORMATION: ZM197M.PB7 SVPC6 V1/V2 DNA sequence -continued

<400> SEQUENCE: 14

```
atggggggg ctgccgccag gttgggggcc gtgattttgt ttgtcgtcat agtgggcctc     60

catggggtcc gcggcaaata tgccttggcg gatgcctctc tcaagatggc cgaccccaat    120

cgatttcgcg gcaaagacct tccggtcctg gaccagctgc tcgaggtacc actaaagccc    180

tgtgtaaagc tgaccccact ctgtgtcact ttaaattgta gtgatgctac cagtaatact    240

accaaaaatg ctaccaatac taataccacc agtacagata acagaaatgc taccagtaat    300

gatactgaaa tgaagggaga aataaaagat tgcactttca atataaccac agaagtaaga    360

gataggaaga caaaacaaag ggcacttttt tataaacttg atgtagtgcc acttgaggag    420

gaaaagaata gctctagtaa aaatagtagc tataaggagt atagattaat aagttgtaat    480

acctcaacca taacacaagc ctgtccaaag tag                                 513
```

<210> SEQ ID NO 15
<211> LENGTH: 420
<212> TYPE: DNA
<213> ORGANISM: Artificial Sequence
<220> FEATURE:
<223> OTHER INFORMATION: ZM53M.PB12 SVPC11 V1/V2 DNA sequence

<400> SEQUENCE: 15

```
atggggggg ctgccgccag gttgggggcc gtgattttgt ttgtcgtcat agtgggcctc     60

catggggtcc gcggcaaata tgccttggcg gatgcctctc tcaagatggc cgaccccaat    120

cgatttcgcg gcaaagacct tccggtcctg gaccagctgc tcgaggtacc actaaaacca    180

tgtgtaaaat tgaccccact ctgtgtcact ttaaactgca gcaagcttaa taatgccacg    240

gatggagaaa tgaaaaattg ctctttcaat gcaaccacag aactaagaga taagaaaaag    300

caagtgtatg cactttttta taaacttgat atagtaccac ttgatggaag aaataactct    360

agtgagtata gattaataaa ttgtaatacc tcaaccataa cacaagcctg tccaaagtag    420
```

<210> SEQ ID NO 16
<211> LENGTH: 141
<212> TYPE: PRT
<213> ORGANISM: Artificial Sequence
<220> FEATURE:
<223> OTHER INFORMATION: ZM233M.PB6 SVPC9 V1/V2 Protein sequence

<400> SEQUENCE: 16

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Asp Cys Ser Thr Tyr Asn Asn Thr His
65                  70                  75                  80

Asn Ile Ser Lys Glu Met Lys Ile Cys Ser Phe Asn Met Thr Thr Glu
                85                  90                  95

Leu Arg Asp Lys Lys Arg Lys Val Asn Val Leu Phe Tyr Lys Leu Asp
            100                 105                 110
```

-continued

```
Leu Val Pro Leu Thr Asn Ser Ser Asn Thr Thr Asn Tyr Arg Leu Ile
        115                 120                 125

Ser Cys Asn Thr Ser Thr Ile Thr Gln Ala Cys Pro Lys
    130                 135                 140


<210> SEQ ID NO 17
<211> LENGTH: 144
<212> TYPE: PRT
<213> ORGANISM: Artificial Sequence
<220> FEATURE:
<223> OTHER INFORMATION: ZM109F.PB4 SVPC13 V1/V2 Protein sequence

<400> SEQUENCE: 17

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Asn Cys Thr Ser Pro Ala Ala His Asn
65                  70                  75                  80

Glu Ser Glu Thr Arg Val Lys His Cys Ser Phe Asn Ile Thr Thr Asp
                85                  90                  95

Val Lys Asp Arg Lys Gln Lys Val Asn Ala Thr Phe Tyr Asp Leu Asp
            100                 105                 110

Ile Val Pro Leu Ser Ser Ser Asp Asn Ser Ser Asn Ser Ser Leu Tyr
        115                 120                 125

Arg Leu Ile Ser Cys Asn Thr Ser Thr Ile Thr Gln Ala Cys Pro Lys
    130                 135                 140


<210> SEQ ID NO 18
<211> LENGTH: 144
<212> TYPE: PRT
<213> ORGANISM: Artificial Sequence
<220> FEATURE:
<223> OTHER INFORMATION: CAP45.2.00.G3 SVPC16 V1/V2 Protein sequence

<400> SEQUENCE: 18

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Arg Cys Thr Asn Ala Thr Ile Asn Gly
65                  70                  75                  80

Ser Leu Thr Glu Glu Val Lys Asn Cys Ser Phe Asn Ile Thr Thr Glu
                85                  90                  95

Leu Arg Asp Lys Lys Gln Lys Ala Tyr Ala Leu Phe Tyr Arg Pro Asp
            100                 105                 110

Val Val Pro Leu Asn Lys Asn Ser Pro Ser Gly Asn Ser Ser Glu Tyr
        115                 120                 125

Ile Leu Ile Asn Cys Asn Thr Ser Thr Ile Thr Gln Ala Cys Pro Lys
    130                 135                 140
```

<210> SEQ ID NO 19
<211> LENGTH: 153
<212> TYPE: PRT
<213> ORGANISM: Artificial Sequence
<220> FEATURE:
<223> OTHER INFORMATION: Bal.01 V1/V2 Protein sequence

<400> SEQUENCE: 19

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Asn Cys Thr Asp Leu Arg Asn Ala Thr
65                  70                  75                  80

Ser Arg Asn Val Thr Asn Thr Thr Ser Ser Ser Arg Gly Met Val Gly
                85                  90                  95

Gly Gly Glu Met Lys Asn Cys Ser Phe Asn Ile Thr Thr Gly Ile Arg
            100                 105                 110

Gly Lys Val Gln Lys Glu Tyr Ala Leu Phe Tyr Glu Leu Asp Ile Val
        115                 120                 125

Pro Ile Asp Asn Lys Ile Asp Arg Tyr Arg Leu Ile Ser Cys Asn Thr
    130                 135                 140

Ser Val Ile Thr Gln Ala Cys Pro Lys
145                 150
```

<210> SEQ ID NO 20
<211> LENGTH: 170
<212> TYPE: PRT
<213> ORGANISM: Artificial Sequence
<220> FEATURE:
<223> OTHER INFORMATION: ZM197M.PB7 SVPC6 V1/V2 Protein sequence

<400> SEQUENCE: 20

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Asn Cys Ser Asp Ala Thr Ser Asn Thr
65                  70                  75                  80

Thr Lys Asn Ala Thr Asn Thr Asn Thr Thr Ser Thr Asp Asn Arg Asn
                85                  90                  95

Ala Thr Ser Asn Asp Thr Glu Met Lys Gly Glu Ile Lys Asp Cys Thr
            100                 105                 110

Phe Asn Ile Thr Thr Glu Val Arg Asp Arg Lys Thr Lys Gln Arg Ala
        115                 120                 125

Leu Phe Tyr Lys Leu Asp Val Val Pro Leu Glu Glu Glu Lys Asn Ser
    130                 135                 140
```

-continued

```
Ser Ser Lys Asn Ser Ser Tyr Lys Glu Tyr Arg Leu Ile Ser Cys Asn
145                 150                 155                 160

Thr Ser Thr Ile Thr Gln Ala Cys Pro Lys
                165                 170


<210> SEQ ID NO 21
<211> LENGTH: 139
<212> TYPE: PRT
<213> ORGANISM: Artificial Sequence
<220> FEATURE:
<223> OTHER INFORMATION: ZM53M.PB12 SVPC11 V1/V2 Protein sequence

<400> SEQUENCE: 21

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Leu Lys Pro Cys Val Lys Leu
    50                  55                  60

Thr Pro Leu Cys Val Thr Leu Asn Cys Ser Lys Leu Asn Asn Ala Thr
65                  70                  75                  80

Asp Gly Glu Met Lys Asn Cys Ser Phe Asn Ala Thr Thr Glu Leu Arg
                85                  90                  95

Asp Lys Lys Lys Gln Val Tyr Ala Leu Phe Tyr Lys Leu Asp Ile Val
            100                 105                 110

Pro Leu Asp Gly Arg Asn Asn Ser Ser Glu Tyr Arg Leu Ile Asn Cys
        115                 120                 125

Asn Thr Ser Thr Ile Thr Gln Ala Cys Pro Lys
    130                 135
```